United States Patent
Zhang et al.

(10) Patent No.: US 8,273,723 B2
(45) Date of Patent: Sep. 25, 2012

(54) COMPOSITIONS AND METHODS FOR IMPROVED GLYCOPROTEIN SIALYLATION

(75) Inventors: Min Zhang, St. Louis, MO (US); James S. Ross, St. Louis, MO (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 87 days.

(21) Appl. No.: 12/681,699

(22) PCT Filed: Oct. 13, 2008

(86) PCT No.: PCT/US2008/079695
§ 371 (c)(1),
(2), (4) Date: Jun. 29, 2010

(87) PCT Pub. No.: WO2009/049284
PCT Pub. Date: Apr. 16, 2009

(65) Prior Publication Data
US 2010/0291624 A1    Nov. 18, 2010

Related U.S. Application Data

(60) Provisional application No. 60/979,483, filed on Oct. 12, 2007.

(51) Int. Cl.
*C12N 15/11* (2006.01)
*C12N 5/00* (2006.01)
*C12N 5/02* (2006.01)
*C12N 15/00* (2006.01)
*C07H 21/02* (2006.01)
*C12P 21/06* (2006.01)

(52) U.S. Cl. ............... 514/44 A; 435/69.1; 435/455; 435/325; 536/23.1

(58) Field of Classification Search .......... 514/44 A; 435/455, 325, 69.1; 536/23.1
See application file for complete search history.

(56) References Cited

U.S. PATENT DOCUMENTS

| | | | |
|---|---|---|---|
| 5,510,261 | A | 4/1996 | Goochee et al. |
| 5,928,915 | A | 7/1999 | Warner et al. |
| 6,436,687 | B1 | 8/2002 | Yu et al. |
| 6,562,588 | B2 | 5/2003 | Warner et al. |
| 6,916,916 | B2 | 7/2005 | Warner et al. |
| 2003/0148493 | A1 | 8/2003 | Warner et al. |

FOREIGN PATENT DOCUMENTS

| | | |
|---|---|---|
| EP | 0700443 | 12/1998 |
| WO | 2006113743 | 10/2006 |
| WO | 2007102432 A1 | 9/2007 |

OTHER PUBLICATIONS

Q6MG70_Rat, UniProt [online] Bethesda, MD USA: United States National Library of Medicine [retrieved on Nov. 10, 2011]. Retrieved from: PubMed.*
Altschul et al., "Basic Local Alignment Search Tool", Journal of Molecular Biology, 1990, pp. 403-410, vol. 215.
Altschul et al., "Gapped BLAST and PSI-BLAST: a new generation of protein database search programs", Nucleic Acids Research, 1997, pp. 3389-3402, vol. 25, No. 17.
Capecchi, High efficiency transformation by direct microinjection of DNA into cultured mammalian cells, Cell, 1980, pp. 479-488, vol. 22, (2 Pt. 2).
Ferrari et al., "Cloning and expression of soluble sialidase from Chinese hamster ovary cells: sequence alignment similarities to bacterial sialidases", Glycobiology, 1994, pp. 367-373, vol. 4, No. 3.
Gramer, "Glycosidase activities in Chinese hamster ovary cell lysate and cell culture supernatant", Biotechnology Progress, 1993, pp. 366-373, vol. 9, No. 4.
Accession No. 035657, dated Nov. 16, 2001, 5 pages.
Karlin et al., "Methods for assessing the statistical significance of molecular sequence features by using general scoring schemes", Proceeding of the National Academy of Sciences, 1990, pp. 2264-2268, vol. 87.
Monti et al., "Expression of a novel human sialidase encoded by the NEU2 gene", Glycobiology, 1999, pp. 1313-1321, vol. 9, No. 12.
Ngantung et al., "RNA interference of sialidase improves glycoprotein sialic acid content consistency", Biotechnology and Bioengineering, 2006, vol. 95, No. 1, pp. 106-119.
Smithies, Targeted gene duplication and disruption for analyzing quantitative genetic traits in mice, Proceedings of the National Academy of Sciences, 1994, pp. 2612-2615, vol. 91, No. 9.
International Search Report for PCT/US08/79695 dated Apr. 22, 2009, 6 pages.
Carrillo, M. et al., "Cloning and characterization of a sialidase from the murine histocompatibility-2 complex low levels of mRNA and a single amino acid mutation are responsible for reduced sialidase activity in mice carrying the Neu+alpha allele," Glycobiology, Jan. 1, 1997, pp. 975-986, vol. 7, No. 7.
Extended European Search Report for European Patent Application No. 08838267.6, Mar. 9, 2012, 12 pages.
Hasegawa, T., et al., "Differential Expression of Three Sialidase Genes in rat Development," Biochem. and Biophys. Res. Comm., Jan. 26, 2001, pp. 726-732, vol. 280, No. 3.
Miyagi, T., et al., "Biochemical and Immunological Studies on Two Distinct Ganglioside-Hydrolyzing Sialidases from the Particulate Fraction of Rat Brain," J. Biochem., May 1, 1990, pp. 787-793, vol. 107, No. 5.
Office Action dated Apr. 18, 2012 from related Chinese Patent Application No. 200880111449.8; 21 pages.

* cited by examiner

*Primary Examiner* — Brian Whiteman
(74) *Attorney, Agent, or Firm* — Polsinelli Shughart PC

(57) ABSTRACT

The present invention provides compositions and methods for the production of glycoproteins with enhanced sialylation. In particular, the invention provides cell lines comprising disrupted sialidase expression and methods of using the cell lines to produce glycoproteins with enhanced sialylation.

32 Claims, 10 Drawing Sheets
(1 of 10 Drawing Sheet(s) Filed in Color)

SEQUENCE LISTING

<160> NUMBER OF SEQ ID NOS: 20

<210> SEQ ID NO 1
<211> LENGTH: 1463
<212> TYPE: DNA

<213> ORGANISM: Cricetulus griseus

<400> SEQUENCE: 1

```
ggggcgagca atggtggcgg cagcacagcc gagcagaccc cgggggccgc cgagcggctg    60
ggcgagccgt cggggtcagg tgctcgcagc gctcttcctg ctgctggcgt ccgtggcggg   120
atccgaggcc agggtgcaag acgacttcag tctggtgcag ccgctggtga ccatggagca   180
gctgctgtgg gtgagcggga ggcagatcgg ctcggtggac actttccgca tcccgctcat   240
caccgccacc cctcggggca cgctcctcgc cttcgccgag gccaggaaaa cgtctgcctc   300
cgatgagggg gccaagttca tcgccatgag gaggtccacg gaccagggta gtacatggtc   360
ctcgacagcc ttcatcgtag acgatgggga ggcctccgac gggctgaacc tgggggccgt   420
ggtgaacgac gtggacacag gggtggtgtt ccttatctat accctgtgtg ctcacaaggt   480
caactgccag gtggcctcca ccatgttggt gtggagtaaa gacgatggca tttcctggag   540
cccaccccga atctctccg tggacattgg cacagaaatg tttgcccctg accaggctc   600
tggcattcag aaacagcggg agcctcggaa gggccggctc attgtgtgtg ccatgggac   660
gctggaacga gatggagtct tttgtctcct cagtgatgac cacggtgcct cgtggcacta   720
cgggactgga gtgagcggca ttcccttcgg ccagcccaaa cacgagcacg atttcaaccc   780
cgacgagtgc cagccctacg agcttccaga tggctctgtc atcatcaatg cccgaaacca   840
gaacaactac cattgccgct gcaggatcgt cctccgcagc tatgatgcct gcgataccct   900
caggccccgg gatgtaacct tcgaccccga gctggtggac cctgtggtag cagcaggagc   960
attagccacc agctcaggca ttgtcttctt ctccaatcca gcccatcctg agttccgagt  1020
gaacctgacc ctgcgctgga gcttcagcaa cggtacgtcc tggcagaagg agagagtcca  1080
ggtgtggccg ggaccagcg gctactcgtc cctgactgcc ctggaaaaca gcacggaggg  1140
agagcagcag cccccgcagc tgttcgttct gtacgagaag ggcctgaacc agtacaccga  1200
gagcatctcc atggtgaaaa tcagtgtcta cggcacgctc tgagcccac cggcgcccaa  1260
ggacactacg cgtcatctga cctcacggct ctccgaggg gctgcagaaa gggcctgaag  1320
cacagctctt cctcgggatg ctagccttt gcagagcagt ttctctttaa cagggaagcc  1380
actccgttag gacctaacag ctgcccagct gcctctccca gacaggaagt tcctcctca  1440
ccaagagcac tttgtagaag gct                                         1463
```

<210> SEQ ID NO 2
<211> LENGTH: 410
<212> TYPE: PRT
<213> ORGANISM: Cricetulus griseus

<400> SEQUENCE: 2

```
Met Val Ala Ala Ala Gln Pro Ser Arg Pro Arg Gly Pro Pro Ser Gly
1               5                   10                  15

Trp Ala Ser Arg Arg Gly Gln Val Leu Ala Ala Leu Phe Leu Leu Leu
            20                  25                  30

Ala Ser Val Ala Gly Ser Glu Ala Arg Val Gln Asp Asp Phe Ser Leu
        35                  40                  45

Val Gln Pro Leu Val Thr Met Glu Gln Leu Trp Val Ser Gly Arg
    50                  55                  60

Gln Ile Gly Ser Val Asp Thr Phe Arg Ile Pro Leu Ile Thr Ala Thr
65                  70                  75                  80

Pro Arg Gly Thr Leu Leu Ala Phe Ala Glu Ala Arg Lys Thr Ser Ala
                85                  90                  95
```

```
Ser Asp Glu Gly Ala Lys Phe Ile Ala Met Arg Arg Ser Thr Asp Gln
            100                 105                 110

Gly Ser Thr Trp Ser Ser Thr Ala Phe Ile Val Asp Gly Glu Ala
        115                 120                 125

Ser Asp Gly Leu Asn Leu Gly Ala Val Val Asn Asp Val Asp Thr Gly
130                 135                 140

Val Val Phe Leu Ile Tyr Thr Leu Cys Ala His Lys Val Asn Cys Gln
145                 150                 155                 160

Val Ala Ser Thr Met Leu Val Trp Ser Lys Asp Gly Ile Ser Trp
                165                 170                 175

Ser Pro Pro Arg Asn Leu Ser Val Asp Ile Gly Thr Glu Met Phe Ala
            180                 185                 190

Pro Gly Pro Gly Ser Gly Ile Gln Lys Gln Arg Glu Pro Arg Lys Gly
        195                 200                 205

Arg Leu Ile Val Cys Gly His Gly Thr Leu Glu Arg Asp Gly Val Phe
210                 215                 220

Cys Leu Leu Ser Asp Asp His Gly Ala Ser Trp His Tyr Gly Thr Gly
225                 230                 235                 240

Val Ser Gly Ile Pro Phe Gly Gln Pro Lys His Glu His Asp Phe Asn
                245                 250                 255

Pro Asp Glu Cys Gln Pro Tyr Glu Leu Pro Asp Gly Ser Val Ile Ile
            260                 265                 270

Asn Ala Arg Asn Gln Asn Asn Tyr His Cys Arg Cys Arg Ile Val Leu
        275                 280                 285

Arg Ser Tyr Asp Ala Cys Asp Thr Leu Arg Pro Arg Ala Val Thr Phe
290                 295                 300

Asp Pro Glu Leu Val Asp Pro Val Val Ala Ala Gly Ala Leu Ala Thr
305                 310                 315                 320

Ser Ser Gly Ile Val Phe Phe Ser Asn Pro Ala His Pro Glu Phe Arg
                325                 330                 335

Val Asn Leu Thr Leu Arg Trp Ser Phe Ser Asn Gly Thr Ser Trp Gln
            340                 345                 350

Lys Glu Arg Val Gln Val Trp Pro Gly Pro Ser Gly Tyr Ser Ser Leu
        355                 360                 365

Thr Ala Leu Glu Asn Ser Thr Glu Gly Glu Gln Gln Pro Pro Gln Leu
370                 375                 380

Phe Val Leu Tyr Glu Lys Gly Leu Asn Gln Tyr Thr Glu Ser Ile Ser
385                 390                 395                 400

Met Val Lys Ile Ser Val Tyr Gly Thr Leu
                405                 410

<210> SEQ ID NO 3
<211> LENGTH: 1833
<212> TYPE: DNA
<213> ORGANISM: Cricetulus griseus

<400> SEQUENCE: 3
gcgcgtgggc gtggcgtcac ttcagcacgg cgcggtctct ctttcctgcc agctcctgct      60
cagagttgtc agggtctgtc tccgcgtcag tggtttccgt ctccgcttcc ctgcctccat     120
cgccccagcc cttctgcagg tcctcctccg agacctcaag gagagctcag aagccagaga     180
cactagagcc gaagtcatgg aagaagtatc agcctgctcc ctcaacagca tctgttcca      240 gcaggaacac cagaaaggga ccacctaccg gattccagcg ctgctctaca tccctcccag     300
ccacaccttc ctggcctttg cagagaagcg ttcctcaagc aaagacgtag atgctctcca     360
```

```
cctggtgctc aggcgagggg tgatgaaggg ccactctgta gagtggggac ccctgcagcc    420
actgatggaa gccacattgc ctgggcatcg gaccatgaac ccctgccctg tatgggagca    480
gagtaccagc cgtgtgttac tgtttttcat ctgtgtgcca gaccgtgtta ctgaacattg    540
gcagattagg tcaggcaaga atgccgcccg tctctgcttc ctgtgcagtc aggatgctgg    600
gtgctcatgg ggtgaagtga aggacttgac tgaggaggtc attggctcag agttgaagca    660
ctgggccaca tttgctgtgg gcccaggcca tggcatccgg ctgcagtcag gaaggctgat    720
cattcccacc tacgcctact atttctcatg caggttcctc tgcttcccgt gttcagtcaa    780
gccccattcc ctgatgatct acagtgatga cttaggagtc acatggcacc atggcaagct    840
cattgggccc caggtgacag gggagtgcca agtggcagaa gtgactggga cgtctggtaa    900
ccttgtgctc tactgcaatg cccggacacc aaacagattc cgagcagaat cttttagtac    960
tgattacggt gactgttttc agaaaccaac cctgaacaca caactctgtg agccccgcta   1020
tggctgccaa ggcagtatag tgagcttcca gcccttgaag atgccattct cacaagaccc   1080
aattggtaaa gctgctccca ctactcagaa gagccctctg ctggacagtt ttctggagcg   1140
ggaggaagga gttggaagac catcaggaac atggctcttg tactcacatc caactagcaa   1200
gaagcggaga attaacctgg gcatctacta caaccggaac cccttggagg tgacctgctg   1260
gtcccgccct tggatcttgc actgtgggcc ctgtggctac tctgatctgg ctgttgtgga   1320
agagcagggc ttatttgcat gtttgtttga atgtgggcag gagcatgagt gtgagcagat   1380
tgccttccgt ctattttcag tccaagaggt tttgagctgt gaagactgca ctggccctag   1440
tagggactaa agccaaatca agcccgatgg gtgaggaccc aactttcctc agaagtgaat   1500
tccaagaggt tttgagctgt gaagactgca ctggccctag tagggactaa agccaaatca   1560
agcccgatgg gtgaggaccc aactttcctc agaagtgaat ccaagagaaa tgtgtgcctt   1620
atcttacaca gcaataaggg tgttgaactg ggagcttgga gacaatggtg tggttttggc   1680
ttgctttagg actgtggata tatcccctga actctgggca tcaggtctcc atttgtaaaa   1740
tgacaagggt ggtttgtgat ttcttgtctt cccattaaaa ggagtgttca cttcttgtcc   1800
cacgaaaaaa aaaaaaaaaa aaaaaaaaaa aaa                                1833
```

<210> SEQ ID NO 4
<211> LENGTH: 417
<212> TYPE: PRT
<213> ORGANISM: Cricetulus griseus

<400> SEQUENCE: 4

```
Met Glu Glu Val Ser Ala Cys Ser Leu Asn Ser Thr Leu Phe Gln Gln
1               5                   10                  15

Glu His Gln Lys Gly Thr Thr Tyr Arg Ile Pro Ala Leu Leu Tyr Ile
            20                  25                  30

Pro Pro Ser His Thr Phe Leu Ala Phe Ala Glu Lys Arg Ser Ser Ser
        35                  40                  45

Lys Asp Val Asp Ala Leu His Leu Val Leu Arg Arg Gly Val Met Lys
    50                  55                  60

Gly His Ser Val Glu Trp Gly Pro Leu Gln Pro Leu Met Glu Ala Thr
65                  70                  75                  80

Leu Pro Gly His Arg Thr Met Asn Pro Cys Pro Val Trp Glu Gln Ser
                85                  90                  95

Thr Ser Arg Val Leu Leu Phe Phe Ile Cys Val Pro Asp Arg Val Thr
            100                 105                 110

Glu His Trp Gln Ile Arg Ser Gly Lys Asn Ala Ala Arg Leu Cys Phe
```

```
                115                 120                 125
Leu Cys Ser Gln Asp Ala Gly Cys Ser Trp Gly Glu Val Lys Asp Leu
    130                 135                 140

Thr Glu Glu Val Ile Gly Ser Glu Leu Lys His Trp Ala Thr Phe Ala
145                 150                 155                 160

Val Gly Pro Gly His Gly Ile Arg Leu Gln Ser Gly Arg Leu Ile Ile
                165                 170                 175

Pro Thr Tyr Ala Tyr Tyr Phe Ser Cys Arg Phe Leu Cys Phe Pro Cys
            180                 185                 190

Ser Val Lys Pro His Ser Leu Met Ile Tyr Ser Asp Asp Leu Gly Val
        195                 200                 205

Thr Trp His His Gly Lys Leu Ile Gly Pro Gln Val Thr Gly Glu Cys
    210                 215                 220

Gln Val Ala Glu Val Thr Gly Thr Ser Gly Asn Leu Val Leu Tyr Cys
225                 230                 235                 240

Asn Ala Arg Thr Pro Asn Arg Phe Arg Ala Glu Ser Phe Ser Thr Asp
                245                 250                 255

Tyr Gly Asp Cys Phe Gln Lys Pro Thr Leu Asn Thr Gln Leu Cys Glu
            260                 265                 270

Pro Arg Tyr Gly Cys Gln Gly Ser Ile Val Ser Phe Gln Pro Leu Lys
        275                 280                 285

Met Pro Phe Ser Gln Asp Pro Ile Gly Lys Ala Ala Pro Thr Thr Gln
    290                 295                 300

Lys Ser Pro Leu Leu Asp Ser Phe Leu Glu Arg Glu Glu Gly Val Gly
305                 310                 315                 320

Arg Pro Ser Gly Thr Trp Leu Leu Tyr Ser His Pro Thr Ser Lys Lys
                325                 330                 335

Arg Arg Ile Asn Leu Gly Ile Tyr Tyr Asn Arg Asn Pro Leu Glu Val
            340                 345                 350

Thr Cys Trp Ser Arg Pro Trp Ile Leu His Cys Gly Pro Cys Gly Tyr
        355                 360                 365

Ser Asp Leu Ala Val Val Glu Glu Gln Gly Leu Phe Ala Cys Leu Phe
    370                 375                 380

Glu Cys Gly Gln Glu His Glu Cys Glu Gln Ile Ala Phe Arg Leu Phe
385                 390                 395                 400

Ser Val Gln Glu Val Leu Ser Cys Glu Asp Cys Thr Gly Pro Ser Arg
                405                 410                 415

Asp

<210> SEQ ID NO 5
<211> LENGTH: 379
<212> TYPE: PRT
<213> ORGANISM: Cricetulus griseus

<400> SEQUENCE: 5

Met Ala Thr Cys Pro Val Leu Gln Lys Glu Thr Leu Phe Gln Thr Gly
1               5                   10                  15

Asp Tyr Ala Tyr Arg Ile Pro Ala Leu Ile Tyr Leu Ser Lys Gln Lys
                20                  25                  30

Thr Leu Leu Ala Phe Ala Glu Lys Arg Leu Thr Lys Thr Asp Glu His
            35                  40                  45

Ala Asp Leu Phe Val Leu Arg Arg Gly Ser Tyr Asn Ala Asp Thr His
        50                  55                  60

Gln Val Gln Trp Gln Ala Glu Glu Val Val Thr Gln Ala Tyr Leu Glu
65                  70                  75                  80
```

-continued

```
Gly His Arg Ser Met Ser Pro Cys Pro Leu Tyr Asp Lys Gln Thr Arg
                85                  90                  95

Thr Leu Phe Leu Phe Phe Ile Ala Val Arg Gly Gln Ile Ser Glu His
            100                 105                 110

His Gln Leu Gln Thr Gly Val Asn Val Thr Arg Leu Cys His Ile Thr
        115                 120                 125

Ser Thr Asp His Gly Lys Thr Trp Ser Ala Val Gln Asp Leu Thr Asp
    130                 135                 140

Thr Thr Ile Gly Ser Thr His Gln Asp Trp Ala Thr Phe Gly Val Gly
145                 150                 155                 160

Pro Gly His Cys Leu Gln Leu Arg Asn Thr Ala Gly Ser Leu Leu Val
                165                 170                 175

Pro Ala Tyr Ala Tyr Arg Lys Gln Pro Ile His Ala Pro Ala Pro
            180                 185                 190

Ser Ala Phe Cys Phe Leu Ser His Asp His Gly Ser Thr Trp Glu Leu
        195                 200                 205

Gly His Phe Val Ser Gln Asn Ser Leu Glu Cys Gln Val Ala Glu Val
    210                 215                 220

Gly Thr Gly Ala Glu Arg Val Val Tyr Leu Asn Ala Arg Ser Cys Leu
225                 230                 235                 240

Gly Ala Arg Val Gln Ala Gln Ser Pro Asn Ser Gly Leu Asp Phe Gln
                245                 250                 255

Asp Asn Gln Val Val Ser Lys Leu Val Glu Pro Pro Lys Gly Cys His
            260                 265                 270

Gly Ser Val Ile Ala Phe Pro Asn Pro Thr Ser Lys Ala Asp Ala Leu
        275                 280                 285

Asp Val Trp Leu Leu Tyr Thr His Pro Thr Asp Ser Arg Lys Arg Thr
    290                 295                 300

Asn Leu Gly Val Tyr Leu Asn Gln Lys Pro Leu Asp Pro Thr Thr Trp
305                 310                 315                 320

Ser Ala Pro Thr Leu Leu Ala Thr Gly Ile Cys Ala Tyr Ser Asp Leu
                325                 330                 335

Gln Asn Met Gly His Gly Pro Asp Gly Ser Pro Gln Phe Gly Cys Leu
            340                 345                 350

Tyr Glu Ser Asn Asn Tyr Glu Glu Ile Val Phe Leu Met Phe Thr Leu
        355                 360                 365

Lys Gln Ala Phe Pro Ala Val Phe Gly Ala Gln
    370                 375

<210> SEQ ID NO 6
<211> LENGTH: 21
<212> TYPE: DNA
<213> ORGANISM: Cricetulus griseus

<400> SEQUENCE: 6 ggguqcaaga cgacuucagt t                                               21

<210> SEQ ID NO 7
<211> LENGTH: 21
<212> TYPE: DNA
<213> ORGANISM: Cricetulus griseus

<400> SEQUENCE: 7
cugaagucgu cuugcaccct t                                               21

<210> SEQ ID NO 8
```

```
<211> LENGTH: 21
<212> TYPE: DNA
<213> ORGANISM: Cricetulus griseus

<400> SEQUENCE: 8
ugggacgcug gaacgagaut t                                              21

<210> SEQ ID NO 9
<211> LENGTH: 21
<212> TYPE: DNA
<213> ORGANISM: Cricetulus griseus

<400> SEQUENCE: 9
aucucguucc agcgucccat t                                              21

<210> SEQ ID NO 10
<211> LENGTH: 21
<212> TYPE: DNA
<213> ORGANISM: Cricetulus griseus

<400> SEQUENCE: 10
ggacacuacg cgucaucugt t                                              21

<210> SEQ ID NO 11
<211> LENGTH: 21
<212> TYPE: DNA
<213> ORGANISM: Cricetulus griseus

<400> SEQUENCE: 11
cagaugacgc guagugucct t                                              21

<210> SEQ ID NO 12
<211> LENGTH: 21
<212> TYPE: DNA
<213> ORGANISM: Cricetulus griseus

<400> SEQUENCE: 12
ccugggugug uaccucaaut t                                              21

<210> SEQ ID NO 13
<211> LENGTH: 21
<212> TYPE: DNA
<213> ORGANISM: Cricetulus griseus

<400> SEQUENCE: 13
auugagguac acacccaggt t                                              21

<210> SEQ ID NO 14
<211> LENGTH: 21
<212> TYPE: DNA
<213> ORGANISM: Cricetulus griseus

<400> SEQUENCE: 14
gacggaugag caugcagaut t                                              21

<210> SEQ ID NO 15
<211> LENGTH: 21
<212> TYPE: DNA
<213> ORGANISM: Cricetulus griseus

<400> SEQUENCE: 15
aucugcaugc ucauccguct t                                              21

<210> SEQ ID NO 16
```

```
<211> LENGTH: 21
<212> TYPE: DNA
<213> ORGANISM: Cricetulus griseus

<400> SEQUENCE: 16
gggaccaccu accggauuct t                                              21

<210> SEQ ID NO 17
<211> LENGTH: 21
<212> TYPE: DNA
<213> ORGANISM: Cricetulus griseus

<400> SEQUENCE: 17
gaauccggua ggugguccct t                                              21

<210> SEQ ID NO 18
<211> LENGTH: 21
<212> TYPE: DNA
<213> ORGANISM: Cricetulus griseus

<400> SEQUENCE: 18
guaccagccg uguguuacut t                                              21

<210> SEQ ID NO 19
<211> LENGTH: 21
<212> TYPE: DNA
<213> ORGANISM: Cricetulus griseus

<400> SEQUENCE: 19
aguaacacac ggcugguact t                                              21

<210> SEQ ID NO 20
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 20

Asp Tyr Lys Asp Asp Asp Asp Lys
1               5
```

COMPOSITIONS AND METHODS FOR IMPROVED GLYCOPROTEIN SIALYLATION

FIELD OF THE INVENTION

The present invention generally relates to sialidases. In particular, the invention relates to compositions and methods for improving the sialylation of glycoproteins.

BACKGROUND OF THE INVENTION

Glycoproteins produced by mammalian cell culture using recombinant DNA technology represent an important category of therapeutic pharmaceuticals for human health care. The biological functions of glycoproteins are often highly dependent upon their carbohydrate structures. Of the numerous sugars found in glycoproteins, the terminal sialic acid is considered particularly important. Sialic acid has been found to influence the solubility, thermal stability, resistance to protease attack, antigenicity, and specific activity of various glycoproteins. The amount of sialic acid in a glycoprotein is the result of two opposing process, i.e., the intracellular addition of sialic acid by sialytransferase activity and the extracellular removal of sialic acid by sialidase cleavage.

When terminal sialic acid is removed from serum glycoproteins, the desialylated proteins have significantly lower circulatory half-lives as compared to the sialylated counterparts. Removal of sialic acid from other glycoptoteins correlates with decreased biological activity and increased serum clearance. Additionally, during the production of glycoproteins by cells in batch culture, nutrient consumption and product accumulation may alter the cellular environment such that protein glycosylation decreases over time. Furthermore, the resultant glycoproteins tend to have glycoform heterogeneity and there is significant batch-to-batch variation in the production processes. Such changes are unacceptable in a bioprocess used for the large-scale production of protein therapeutic agents. Therefore, in mammalian cell culture systems it is often desirable to maximize the final sialic acid content of a glycoprotein product to ensure its quality and consistency as an effective pharmaceutical. A need exists, therefore, for a mammalian cell culture system that has enhanced glycoprotein sialylation. Such a system would improve the production of adequately sialylated recombinant glycoproteins.

SUMMARY OF THE INVENTION

Among the various aspects of the invention is the provision of a cell line comprising disrupted expression of at least one chromosomally integrated nucleic acid sequence encoding a non-cytoplasmic sialidase. The amino acid sequence of the non-cytoplasmic sialidase whose expression is disrupted is selected from the group consisting of (a) at least about 95% identical to SEQ ID NO:2, and (b) at least about 80% identical to SEQ ID NO:4.

Another aspect of the invention encompasses a method for producing a glycoprotein. The method comprises expressing a nucleic acid sequence encoding the glycoprotein in a cell comprising disrupted expression of at least one chromosomally integrated nucleic acid sequence encoding a non-cytoplasmic sialidase, wherein the glycoprotein has increased sialylation relative to a suitable control. The amino acid sequence of the non-cytoplasmic sialidase whose expression is disrupted in the cell is selected from the group consisting of (a) at least about 95% identical to SEQ ID NO:2, and (b) at least about 80% identical to SEQ ID NO:4.

A further aspect of the invention provides an isolated nucleic acid encoding a polypeptide whose amino acid sequence consists of SEQ ID NO:2.

Still another aspect of the invention encompasses an isolated nucleic acid encoding a polypeptide whose amino acid sequence consists of SEQ ID NO:4.

Another alternate aspect of the invention provides for a purified polypeptide whose the amino acid sequence consists of SEQ ID NO:2.

A further aspect of the invention encompasses a purified polypeptide whose amino acid sequence consists of SEQ ID NO:4.

Other aspects and features of the invention are described in more below.

REFERENCE TO COLOR FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
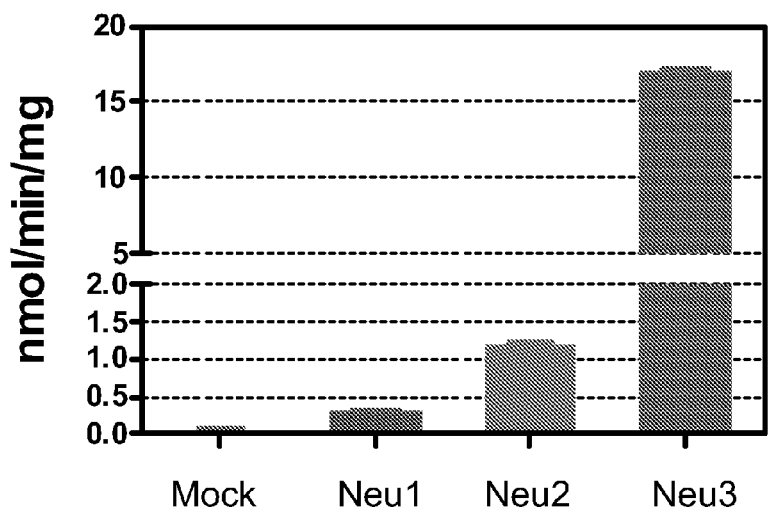
FIG. 1 illustrates the sialidase activity of the proteins encoded by the CHO Neu1, Neu2, and Neu3 genes. Presented is the enzyme activity in lysates of cells transfected with expression constructs containing the coding region of each gene, as indicated (or any empty expression construct).

Sialidases are enzymes that remove the terminal sialic acid residue from glycoproteins and glycolipids. Chinese hamster ovary (CHO) cells are known to contain a cytoplasmic sialidase. The inventors of the present invention have isolated and characterized two additional sialidases in CHO cells, i.e., a lysosomal sialidase and a plasma membrane-associated sialidase. Accordingly, the present invention provides cell lines comprising disrupted expression of the two newly identified sialidase genes, either alone, in combination with each other, or in combination with the cytoplasmic sialidase. The invention also provides methods for producing glycoproteins of interest using cells comprising disrupted sialidase expression. In general, glycoproteins produced by the methods of the invention have increased sialic acid content relative to those produced in parental cells having normal sialidase activity.

(I) Non-cytoplasmic Sialidases

One aspect of the present invention encompasses an isolated nucleic acid sequence encoding a polypeptide whose amino acid sequence consists of SEQ ID NO:2. In general, the isolated nucleic acid sequence is at least about 80% identical to SEQ ID NO:1. In some embodiments, isolated nucleic acid sequence may be about 80, 81, 82, 83, 84, 85, 86, 87, 88, 89, 90, 91, 92, 93, 94, 95, 96, 97, 98, 99, or 99.5% identical to SEQ ID NO:1. In other embodiments, the isolated nucleic acid sequence may consist essentially of SEQ ID NO:1. In these embodiments, there may be additional extraneous nucleotides sequences flanking the 5' end, 3' end, or both ends of the isolated nucleic acid sequence. The extraneous nucleotides sequences may be linkers comprising restriction endonuclease cleavage sites for cloning, linkers that are complementary to primers for amplification and/or other detection methods, and the like. In still other embodiments, the isolated nucleic acid sequence may consist of SEQ ID NO:1.

Another aspect of the invention provides an isolated nucleic acid sequence encoding a polypeptide whose amino acid sequence consists of SEQ ID NO:4. In general, the isolated nucleic acid sequence is at least about 80% identical to SEQ ID NO:3. In some embodiment, isolated nucleic acid sequence may be about 80, 81, 82, 83, 84, 85, 86, 87, 88, 89, 90, 91, 92, 93, 94, 95, 96, 97, 98, 99, or 99.5% identical to SEQ ID NO:3. In other embodiments, the isolated nucleic acid sequence may consist essentially of SEQ ID NO:3. In these embodiments, there may be additional extraneous nucleotides sequences flanking the 5' end, 3' end, or both ends of the isolated nucleic acid sequence. The extraneous nucleotides sequences may be linkers comprising restriction endonuclease cleavage sites for cloning, linkers that are complementary to primers for amplification and/or other detection methods, and the like. In still other embodiments, the isolated nucleic acid sequence may consist of SEQ ID NO:3.

A further aspect of the invention encompasses a purified polypeptide whose amino acid sequence may be at least about 95% identical to the amino acid sequence of SEQ ID NO:2, wherein the purified polypeptide has sialidase enzyme activity. In some embodiments, the amino acid sequence of the purified polypeptide may be about 95, 96, 97, 98, 99, or 99.5% identical to the amino acid sequence of SEQ ID NO:2. In other embodiments, the amino acid sequence of the purified polypeptide may consist essentially of SEQ ID NO:2. In these embodiments, there may be extraneous amino acid sequences flanking the amino-terminal end, carboxyl-terminal end, or both ends of the purified polypeptide, wherein the biological activity of the purified polypeptide is not altered. These extraneous amino acid sequences may include, but are not limited to, an antibody epitope tag, such as a FLAG tag, a myc tag, a 6×His tag, an HA tag, a GST tag, a HSV tag, and the like. In a further embodiment, the amino acid sequence of the purified polypeptide may consist of SEQ ID NO:2. Typically the polypeptide encoded by SEQ ID NO:2 (or a related polypeptide) is localized to the lysosomes of a eukaryotic cell.

Still another aspect of the invention provides a purified polypeptide whose amino acid sequence may be at least about 80% identical to the amino acid sequence of SEQ ID NO:4, wherein the purified polypeptide has sialidase enzyme activity. In some embodiments, the amino acid sequence of the purified polypeptide may be about 80, 81, 82, 83, 84, 85, 86, 87, 88, 89, 90, 91, 92, 93, 94, 95, 96, 97, 98, 99, or 99.5% identical to the amino acid sequence of SEQ ID NO:4. In other embodiments, the amino acid sequence of the purified polypeptide may consist essentially of SEQ ID NO:4. In these embodiments, there may be extraneous amino acid sequences flanking the amino-terminal end, carboxyl-terminal end, or both ends of the purified polypeptide, wherein the biological activity of the purified polypeptide is not altered. These extraneous amino acid sequences may include, but are not limited to, an antibody epitope tag, such as a FLAG tag, a myc tag, a 6×His tag, an HA tag, a GST tag, a HSV tag, and the like. In a further embodiment, the amino acid sequence of the purified polypeptide may consist of SEQ ID NO:4. Typically the polypeptide encoded by SEQ ID NO:2 (or a related polypeptide) is localized to the plasma membrane of a eukaryotic cell.

(II) Cell Lines Comprising Disrupted Sialidase Expression

Another aspect of the invention provides cell lines in which the expression of at least one endogenous, chromosomally integrated nucleic acid sequence encoding a non-cytoplasmic sialidase is disrupted, such that the cell line has reduced sialidase enzyme activity. The cell lines may further comprise disrupted expression of an endogenous, chromosomally integrated nucleic acid sequence encoding a cytoplasmic sialidase.

In some embodiments, the cell line comprises disrupted expression of at least one chromosomally integrated nucleic acid sequence encoding a non-cytoplasmic sialidase, wherein the amino acid sequence of the sialidase is selected from the group consisting of (a) at least about 95% identical to SEQ ID NO:2, and (b) at least about 80% identical to SEQ ID NO:4. In some embodiments, the non-cytoplasmic sialidase whose expression is disrupted may be about 95, 96, 97, 98, 99, or 99.5% identical to SEQ ID NO:2. In another embodiment, the non-cytoplasmic sialidase whose expression is disrupted may consist essentially of SEQ ID NO:2. In a further embodiment, the non-cytoplasmic sialidase whose expression is disrupted may consist of SEQ ID NO:2. In other embodiments, the non-cytoplasmic sialidase whose expression is disrupted may be about 80, 81, 82, 83, 84, 85, 86, 87, 88, 89, 90, 91, 92, 93, 94, 95, 96, 97, 98, 99, or 99.5% identical to the amino acid sequence of SEQ ID NO:4. In an alternate embodiment, the non-cytoplasmic sialidase whose expression is disrupted may consist essentially of SEQ ID NO:4. In a further embodiment, the non-cytoplasmic sialidase whose expression is disrupted may consist of SEQ ID NO:4.

In some iterations, the cell line may have disrupted expression of one non-cytoplasmic sialidase. For example, the expression of the lysosomal sialidase (i.e., related to SEQ ID NO:2) may be disrupted. Alternatively, the expression of the plasma membrane-associated sialidase (i.e., related to SEQ ID NO:4) may be disrupted. In other iterations, the cell line may have disrupted expression of both non-cytoplasmic sialidases. That is, the expression of the lysosomal sialidase (i.e., related to SEQ ID NO:2) and the plasma membrane-associated sialidase (i.e., related to SEQ ID NO:4) may be both disrupted.

In alternate embodiments, the cell line may further comprise disrupted of a chromosomally integrated nucleic acid sequence encoding a cytoplasmic sialidase, the amino acid sequence of which may be at least about 85% identical to SEQ ID NO:5. In some embodiments, the cytoplasmic sialidase whose expression is disrupted may be about 85, 86, 87, 88, 89, 90, 91, 92, 93, 94, 95, 96, 97, 98, 99, or 99.5% identical to the amino acid sequence of SEQ ID NO:5. In a further embodiment, the cytoplasmic sialidase whose expression is disrupted may consist essentially of SEQ ID NO:5. In yet another embodiment, the cytoplasmic sialidase whose expression is disrupted may consist of SEQ ID NO:5.

In certain iterations, the cell line may have disrupted expression of one non-cytoplasmic sialidase and the cytoplasmic sialidase. For example, the expression of the lysosomal sialidase (i.e., related to SEQ ID NO:2) and the cytoplasmic (i.e., related to SEQ ID NO:5) may be disrupted. Alternatively, the expression of the plasma membrane-associated sialidase (i.e., related to SEQ ID NO:4) and the cytoplasmic (i.e., related to SEQ ID NO:5) may be disrupted. In certain other iterations, the cell line may have disrupted expression of both non-cytoplasmic sialidases and the cytoplasmic sialidase. That is, the expression of the lysosomal sialidase (i.e., related to SEQ ID NO:2), the plasma membrane-associated sialidase (i.e., related to SEQ ID NO:4)m, and the cytoplasmic (i.e., related to SEQ ID NO:5) all may be disrupted.

(a) Cell Types

In general, eukaryotic cells will be used in the practice of the invention. Suitable host cells include fungi or yeast, such as *Pichia pastoris* or *Saccharomyces cerevisiae*; insect cells, such as SF9 cells from *Spodoptera frugiperda* or S2 cells from *Drosophila melanogaster*; plant cells; and animal cells, such as mouse, rat, hamster, non-human primate, or human cells. Examples of suitable cell lines include Chinese hamster ovary (CHO) cells, monkey kidney CVI line transformed by SV40 (COS7); human embryonic kidney line 293; baby hamster kidney cells (BHK); mouse sertoli cells (TM4); monkey kidney cells (CVI-76); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor cells (MMT); rat hepatoma cells (HTC); HIH/3T3 cells, and TRI cells. For an extensive list of mammalian cell lines, those of ordinary skill in the art may refer to the American Type Culture Collection catalog (ATCC®, Mamassas, Va.). In general, the cells may be of a variety of cell types, e.g., fibroblast, myoblast, T or B cell, macrophage, epithelial cell, and so forth. In preferred embodiments, the cells are of a type that is widely used for the production of glycoproteins. In an exemplary embodiment, the cells may be CHO cells. Numerous CHO cell lines, some of which produce a glycoprotein of interest, are available from ATCC. Examples of CHO cells that stably express a glycoprotein of interest include CHO-ICAM-1 cells, which produce intracellular cell adhesion molecule-1, and CHO-hIFNγ cells, which produce human interferon gamma.

(b) Disrupted Expression

In general, the cell lines of the invention have reduced sialidase expression. The expression may be disrupted at several different steps during gene expression. For example, the DNA sequence encoding the sialidase polypeptide may be altered such that functional messenger RNA (mRNA) (and, consequently, a functional polypeptide) is not made. Alternatively, the mRNA may be altered (or degraded) such that the polypeptide is not made or reduced levels of the polypeptide are made.

(i) RNA Interference

Sialidase expression may be disrupted using an RNA interference (RNAi) agent that inhibits expression of a target mRNA or transcript. The RNAi agent may lead to cleavage of the target transcript. Alternatively, the RNAi agent may prevent or disrupt translation of the target transcript into a protein.

In some embodiments, the RNAi agent may be a short interfering RNA (siRNA). In general, a siRNA comprises a double-stranded RNA molecule that ranges from about 15 to about 29 nucleotides in length. The siRNA may be about 16-18, 17-19, 21-23, 24-27, or 27-29 nucleotides in length. In a preferred embodiment, the siRNA may be about 21 nucleotides in length. The siRNA may optionally further comprise one or two single-stranded overhangs, e.g., a 3' overhang on one or both ends. The siRNA may be formed from two RNA molecules that hybridize together or, alternatively, may be generated from a short hairpin RNA (shRNA) (see below). In some embodiments, the two strands of the siRNA may be completely complementary, such that no mismatches or bulges exist in the duplex formed between the two sequences. In other embodiments, the two strands of the siRNA may be substantially complementary, such that one or more mismatches and/or bulges may exist in the duplex formed between the two sequences. In certain embodiments, one or both of the 5' ends of the siRNA may have a phosphate group, while in other embodiments one or both of the 5' ends may lack a phosphate group. In other embodiments, one or both of the 3' ends of the siRNA may have a hydroxyl group, while in other embodiments one or both of the 5' ends may lack a hydroxyl group.

One strand of the siRNA, which is referred to as the "antisense strand" or "guide strand," includes a portion that hybridizes with the target transcript. In preferred embodiments, the antisense strand of the siRNA may be completely complementary with a region of the target transcript, i.e., it hybridizes to the target transcript without a single mismatch or bulge over a target region between about 15 and about 29 nucleotides in length, preferably at least 16 nucleotides in length, and more preferably about 18-20 nucleotides in length. In other embodiments, the antisense strand may be substantially complementary to the target region, i.e., one or more mismatches and/or bulges may exist in the duplex formed by the antisense strand and the target transcript. Typically, siRNAs are targeted to exonic sequences of the target transcript. Those of skill in the art are familiar with programs, algorithms, and/or commercial services that design siRNAs for target transcripts. An exemplary example is the Rosetta siRNA Design Algorithm (Rosetta Inpharmatics, North Seattle, WA) and MISSION® siRNA (Sigma-Aldrich, St. Louis, Mo.). The siRNA may be enzymatically synthesized in vitro using methods well known to those of skill in the art. Alternatively, the siRNA may be chemically synthesized using oligonucleotide synthesis techniques that are well known in the art.

In other embodiments, the RNAi agent may be a short hairpin RNA (shRNA). In general, a shRNA is an RNA molecule comprising at least two complementary portions that are hybridized or are capable of hybridizing to form a double-stranded structure sufficiently long to mediate RNA interference (as described above), and at least one single-stranded portion that forms a loop connecting the regions of the shRNA that form the duplex. The structure may also be called a stem-loop structure, with the stem being the duplex portion. In some embodiments, the duplex portion of the structure may be completely complementary, such that no mismatches or bulges exist in the duplex region of the shRNA. In other embodiments, the duplex portion of the structure may be substantially complementary, such that one or more mismatches and/or bulges may exist in the duplex portion of the shRNA. The loop of the structure may be from about 1 to about 20 nucleotides in length, preferably from about 4 to about 10 about nucleotides in length, and more preferably from about 6 to about 9 nucleotides in length. The loop may be located at either the 5' or 3' end of the region that is complementary to the target transcript (i.e., the antisense portion of the shRNA).

The shRNA may further comprise an overhang on the 5' or 3' end. The optional overhang may be from about 1 to about 20 nucleotides in length, and more preferably from about 2 to about 15 nucleotides in length. In some embodiments, the overhang may comprise one or more U residues, e.g., between about 1 and about 5 U residues. In some embodiments, the 5' end of the shRNA may have a phosphate group, while in other embodiments it may not. In other embodiments, the 3' end of the shRNA may have a hydroxyl group, while it other embodiments it may not. In general, shRNAs are processed into siRNAs by the conserved cellular RNAi machinery. Thus, shRNAs are precursors of siRNAs and are similarly capable of inhibiting expression of a target transcript that is complementary of a portion of the shRNA (i.e., the antisense portion of the shRNA). Those of skill in the art are familiar with the available resources (as detailed above) for the design and synthesis of shRNAs. An exemplary example is MISSION® shRNAs (Sigma-Aldrich).

In still other embodiments, the RNAi agent may be an RNAi expression vector. Typically, an RNAi expression vector may be used for intracellular (in vivo) synthesis of RNAi agents, such as siRNAs or shRNAs. In one embodiment, two separate, complementary siRNA strands may be transcribed using a single vector containing two promoters, each of which directs transcription of a single siRNA strand (i.e., each promoter is operably linked to a template for the siRNA so that transcription may occur). The two promoters may be in the same orientation, in which case each is operably linked to a template for one of the complementary siRNA strands. Alternatively, the two promoters may be in opposite orientations, flanking a single template so that transcription for the promoters results in synthesis of two complementary siRNA strands. In another embodiment, the RNAi expression vector may contain a promoter that drives transcription of a single RNA molecule comprising two complementary regions, such that the transcript forms a shRNA.

Those of skill in the art will appreciate that it is preferable for siRNA and shRNA agents to be produced in vivo via the transcription of more than one transcription unit. Generally speaking, the promoters utilized to direct in vivo expression of the one or more siRNA or shRNA transcription units may be promoters for RNA polymerase III (Pol III). Certain Pol III promoters, such as U6 or H1 promoters, do not require cis-acting regulatory elements within the transcribed region, and thus, are preferred in certain embodiments. In other embodiments, promoters for Pol II may be used to drive expression of the one or more siRNA or shRNA transcription units. In some embodiments, tissue-specific, cell-specific, or inducible Pol II promoters may be used.

A construct that provides a template for the synthesis of siRNA or shRNA may be produced using standard recombinant DNA methods and inserted into any of a wide variety of different vectors suitable for expression in eukaryotic cells. Guidance may be found in Current Protocols in Molecular Biology (Ausubel et al., John Wiley & Sons, New York, 2003) or Molecular Cloning: A Laboratory Manual (Sambrook & Russell, Cold Spring Harbor Press, Cold Spring Harbor, N.Y., $3^{rd}$ edition, 2001). Those of skill in the art also appreciate that vectors may comprise additional regulatory sequences (e.g., termination sequence, translational control sequence, etc.), as well selectable marker sequences. DNA plasmids are known in the art, including those based on pBR322, PUC, and so forth. Since many expression vectors already contain a suitable promoter or promoters, it may be only necessary to insert the nucleic acid sequence that encodes the RNAi agent of interest at an appropriate location with respect to the promoter(s). Viral vectors may also be used to provide intracellular expression of RNAi agents. Suitable viral vectors include retroviral vectors, lentiviral vectors, adenoviral vectors, adeno-associated virus vectors, herpes virus vectors, and so forth. In preferred embodiment, the RNAi expression vector is a shRNA lentiviral-based vector or lentiviral particle, such as that provided in MISSION® TRC shRNA products (Sigma-Aldrich).

The RNAi agents or RNAi expression vectors may be introduced into the cell using methods well known to those of skill in the art. Guidance may be found in Ausubel et al., supra or Sambrook & Russell, supra, for example. In some embodiments, the RNAi expression vector, e.g., a viral vector, may be stably integrated into the genome of the cell, such that sialidase expression is disrupted over subsequent cell generations.

(ii) Gene Targeting

In other embodiments, homologous recombination techniques may be used to disrupt sialidase expression at the level of the genomic DNA. Accordingly, these techniques may be used to delete a nucleic acid sequence, delete a portion of a nucleic acid sequence, or introduce point mutations in the nucleic acid sequence, such that no functional product may be made. In one embodiment, the nucleic acid sequence may be targeted by homologous recombination using the techniques of Capecchi (Cell 22:4779-488, 1980) and Smithies (Proc Natl Acad Sci USA 91:3612-3615, 1994). In other embodiments, the nucleic acid sequence may be targeted using a Cre-loxP site-specific recombination system, a Flp-FRT site-specific recombination system, or variants thereof. Such recombination systems are commercially available, and additional guidance may be found in Ausubel et al., supra. In still another embodiment, the gene may be targeted using zinc finger nuclease (ZFN)-mediated gene targeting (Sangamo Biosciences, Richmond, Calif.). Briefly, ZFNs are synthetic proteins comprising an engineered zinc finger DNA-binding domain fused to the cleavage domain of the FokI restriction endonuclease. ZFNs may be used to induce double-stranded breaks in specific DNA sequences and thereby promote site-specific homologous recombination and targeted manipulation of genomic sequences. ZFNs may be engineered to target any DNA sequence of interest.

(iii) Measuring Disrupted Expression

The RNAi and gene targeting methods described above will generally lead to decreased expression of the sialidase gene(s) and, consequently, decreased sialidase enzyme activity. Accordingly, the cells will generally have reduced levels of sialidase mRNA and/or sialidase protein. A wide variety of methods known in the art may be used to measure mRNA levels, protein levels, or enzyme activity. Non-limiting examples of RNA detection methods include reverse transcriptase PCR, reverse transcriptase quantitative PCR, nucleic acid microarrays, hybridization-based methods, branched DNA detection technologies, Northern blotting, and nuclease protection assays. Non-limiting examples of protein detection methods include Western blotting, ELISA assays, and other immunoassays. Depending upon the specificity of the probes used in these detection assays, each type of sialidase may be detected singly or all three may be detected simultaneously. Regardless of the specificity, however, a decrease in the level of expression may be determined by comparing the levels (of mRNA and/or protein) in a cell with disrupted sialidase expression to those in an untreated cell. Preferably the decrease in sialidase expression results in a decrease in sialidase enzyme activity in the cells (e.g., in a lysate obtained from the cells), in the medium in which the cells were cultured, or both. Sialidase enzyme activity may be measured using a variety of sialidase assays known in the art. For example, sialidase activity may be measured using the assay described in Example 2.

In some embodiments, the levels of sialidase mRNA(s) may be reduced by at least 2-fold, at least 5-fold, at least 10-fold, at least 100-fold, at least 1000-fold, or at least 10,000-fold relative to those of untreated cells. In other embodiments, the amount of sialidase protein(s) may be reduced by at least 2-fold, at least 5-fold, at lest 10-fold, at least 100-fold, at least 1000-fold, or at least 10,000-fold relative to that of untreated cells. Furthermore, sialidase enzyme activity may be decreased by between 20% and 50%, between 50% and 60%, between 60% and 70%, between 70% and 80%, between 80% and 90%, or between 90% and 100% of the value in untreated cells.

(c) Preferred Embodiments

Preferably, the cell line comprising disrupted sialidase expression is derived from a CHO cell line. In one embodiment, the CHO cell line comprises disrupted expression of the sialidase consisting of SEQ ID NO:2. In another embodiment, the CHO cell line comprises disrupted expression of the sialidase consisting of SEQ ID NO:4. In still another embodiment, the CHO cell line comprises disrupted expression of the sialidases consisting of SEQ ID NO:2 and SEQ ID NO:4. In a further embodiment, the CHO cell line comprises disrupted expression of the sialidases consisting of SEQ ID NO:2 and SEQ ID NO:5. In yet another embodiment, the CHO cell line comprises disrupted expression of the sialidases consisting of SEQ ID NO:4 and SEQ ID NO:5. In another alternate embodiment, the CHO cell line comprises disrupted expression of the sialidases consisting of SEQ ID NO:2, SEQ ID NO:4, and SEQ ID NO:5. Preferably, sialidase expression is disrupted via RNAi.

(III) Methods for Producing Glycoproteins with Enhanced Sialylation

Still another aspect of the invention provides a method for producing a glycoprotein comprising enhanced sialylation. In general, the method comprises expressing a nucleic acid sequence encoding the glycoprotein of interest in a cell comprising disrupted expression of at least one nucleic acid sequence encoding a non-cytoplasmic sialidase, wherein the glycoprotein produced by the cells has increased sialylation. In other embodiments, the cell further comprises disrupted expression of a nucleic acid encoding a cytoplasmic sialidase. Sialidase-disrupted cells suitable for use in the method of the invention are described above in Section (II).

The glycoprotein produced by a cell with disrupted sialidase expression generally will have higher levels of sialylation than a glycoprotein produced by a control cell in which the expression of a sialidase has not been altered (e.g., the parental cells from which the sialidase-disrupted cells are derived). The sialylation of the glycoprotein produced by the cell with disrupted sialidase(s) expression may at least about 10% greater than that of a glycoprotein produced by a control cell. In some embodiments, the sialylation of the glycoprotein produced by the cell with disrupted sialidase expression may about 10, 20, 30, 40, 50, 60, 70, 80, 90, 100, 150, 200, 250, 300, 350, 400, 450, or 500% greater than that of a glycoprotein produced by control cell. In other embodiments, the sialylation of the glycoprotein produced by the cell with disrupted sialidase expression may be more than about 500% greater than that of a glycoprotein produced by a control cell.

In some embodiments, the sialidase-disrupted cell used for producing the glycoprotein may already express the glycoprotein of interest. For example, the glycoprotein may be endogenous to the cell, whereby the nucleic acid encoding the glycoprotein is present in the genome of the cell. Alternatively, the glycoprotein may be an exogenous to the cell and the acid sequence encoding the glycoprotein may have been stably integrated into a chromosome of the cell. As mentioned above in Section (II)(a), there are commercially available cell lines that express exogenous glycoproteins. For example, the CHO cell line, CHO-hIFNγ, stably expresses human interferon gamma.

In other embodiments, the sialidase-disrupted cell used for producing the glycoprotein may not express the glycoprotein of interest. In such instances, the nucleic acid sequence encoding the glycoprotein of interest may be introduced into the sialidase-disrupted cell. The nucleic acid sequence encoding the glycoprotein of interest may be stably integrated into the genome of the sialidase-disrupted cell. Alternatively, nucleic acid sequence encoding the glycoprotein of interest may be transiently introduced in the sialidase-disrupted. Stated another way, the nucleic acid sequence encoding the glycoprotein of interest may be extrachromosomal. Those of skill in the art are familiar with suitable vectors and methods of introducing nucleic acids into cells. Furthermore, guidance may be found in Ausubel et al., supra or Sambrook & Russell, supra.

Examples of glycoproteins that may be produced by the sialidase-disrupted cells include growth factors, growth factor receptors, cytokines, interleukins and other immune system proteins, interferons, erythropoietin, integrins, addressins, selectins, homing receptors, T cell receptors, immunoglobulins, monoclonal antibodies, soluble major histocompatibility complex antigens, enzymes (e.g., tissue plasminogen activator, streptokinase, cholesterol biosynthetic or degradative enzymes, steroidogenic enzymes, kinases, phosphodiesterases, phosphatases, methylases, de-methylases, dehydrogenases, cellulases, proteases, lipases, phospholipases, aromatases, cytochromes, etc.), hormone or peptide receptors, binding proteins, transcription factors, translation factors, oncoproteins or proto-oncoproteins, muscle proteins, myeloproteins, neuroactive proteins, tumor growth suppressing proteins, anti-sepsis proteins, structural proteins, and blood proteins (e.g., thrombin, serum albumin, Factor VII, Factor VIII, Factor IX, Factor X, Protein C, von Willebrand factor, etc.). In some embodiment, the glycoprotein may comprise a peptide tag, such as an antibody epitope tag (e.g., FLAG tag, HA tag, myc tag, 6×His tag, etc.) In other embodiments, the glycoprotein may be a fusion protein comprising a first domain from a glycoprotein of interest and a second domain from another protein of interest, wherein the two domains either are fused together or separated by one or more additional domains. For example, the first domain may comprise an immunoglobulin domain or portion thereof and the second domain may comprise a non-immunoglobulin polypeptide. The polypeptide or portion thereof may be a naturally occurring polypeptide, it may be an engineered or altered form of a naturally occurring polypeptide, or it may be an artificial or man-made polypeptide.

The method further comprises culturing the sialidase-disrupted cells under conditions whereby the glycoprotein is produced. Those of skill in the art will know the appropriate conditions under which to culture a particular type of cells. In some embodiments, the cells may be grown in small vessels for the production of small amounts of the glycoprotein (e.g., milligrams to grams). In other embodiments, the cells may be maintained in a large bioreactor for the production of large quantities of the glycoprotein (e.g., kilogram quantities). In general, the glycoprotein produced by the sialidase-disrupted cells will have enhanced sialylation relative to the same glycoprotein produced by the same type of cells in which sialidase expression was not disrupted. The amount of sialic acid conjugated to the glycoprotein of interest may be measured by one of several assays known in the art, or with a commercially available kit.

After a period of time, the cells and/or the culture medium will generally be harvested and the glycoprotein of interest may be purified therefrom. Suitable purification methods include affinity chromatography, immunoaffinity chromatography, hydrophobic interaction chromatography, ion exchange chromatography, size exclusion chromatography, precipitation, dialysis, and combinations thereof. See, for example, Roe (ed), Protein Purification Techniques: A Practical Approach, Oxford University Press, $2^{nd}$ edition, 2001. A skilled artisan will be able to select methods appropriate for a particular glycoprotein of interest.

(IV) Kits

Still another aspect of the invention encompasses kits for producing glycoproteins comprising enhanced sialylation. Typically, a kit comprises a cell line of the invention, wherein the cell line comprises disrupted expression of at least one non-cytoplasmic sialidase. In some embodiments, the cell line may further comprise disrupted expression of the cytoplasmic sialidase. Sialidase-disrupted cells suitable for use in the kits of the invention are described above in Section (II). The kits may also comprise instructions for use.

In one embodiment, the kit may further comprise suitable culture media for growing the sialidase-disrupted cells. In another embodiment, the kit may further comprise constructs (e.g., plasmid, viral, etc.) for introducing a nucleic acid sequence encoding the glycoprotein of interest into the sialidase-disrupted cells. In still another embodiment, the kit may also further comprise reagents for detecting and/or purifying the glycoprotein that is produced by the cells of the invention. Non-limiting examples of suitable reagents include PCR primers, polyclonal antibodies, monoclonal antibodies, affinity chromatography media, immunoaffinity chromatography media, and the like.

In a preferred embodiment, the kit comprises a CHO cell line comprising disrupted sialidase expression. In one embodiment, the CHO cell line comprises disrupted expression of the sialidase consisting of SEQ ID NO:2. In another embodiment, the CHO cell line comprises disrupted expression of the sialidase consisting of SEQ ID NO:4. In still another embodiment, the CHO cell line comprises disrupted expression of the sialidases consisting of SEQ ID NO:2 and SEQ ID NO:4. In a further embodiment, the CHO cell line comprises disrupted expression of the sialidases consisting of SEQ ID NO:2 and SEQ ID NO:5. In yet another embodiment, the CHO cell line comprises disrupted expression of the sialidases consisting of SEQ ID NO:4 and SEQ ID NO:5. In another alternate embodiment, the CHO cell line comprises disrupted expression of the sialidases consisting of SEQ ID NO:2, SEQ ID NO:4, and SEQ ID NO:5. Preferably, sialidase expression is disrupted via RNAi.

DEFINITIONS

To facilitate understanding of the invention, several terms are defined below.

As used herein, the term "complementary" refers to the association of double-stranded nucleic acids by base pairing through specific hydrogen bonds (i.e., 5'-A G T C-3' pairs with the complimentary sequence 3'-T C A G-5'). Two single-stranded molecules may be completely complementary, i.e., all the base pairs are complimentary and there are no mismatches. Alternatively, two single-stranded molecules may be substantially complementary, i.e., at least one mismatch exists between the two stands.

The phrase "disrupted expression," as used herein, refers to manipulation of a nucleic acid sequence that codes for a polypeptide such that the polypeptide is not made (i.e., knocked out) or the polypeptide is made at reduced levels (i.e., knocked down). Expression may be disrupted at several levels. For example, the DNA encoding the polypeptide may be altered such that no functional messenger RNA, and hence, no functional protein is made. Alternatively, the messenger RNA may be affected such that none of the polypeptide is made or the polypeptide is made at reduced levels.

The term "hybridization," as used herein, refers to the process of hydrogen bonding, or base pairing, between the bases comprising two complementary single-stranded nucleic acid molecules to form a double-stranded hybrid or duplex. The "stringency" of hybridization is typically determined by the conditions of temperature and ionic strength. Nucleic acid hybrid stability is generally expressed as the melting temperature or Tm, which is the temperature at which the hybrid is 50% denatured under defined conditions. Equations have been derived to estimate the Tm of a given hybrid; the equations take into account the G+C content of the nucleic acid, the nature of the hybrid (e.g., DNA:DNA, DNA:RNA, etc.), the length of the nucleic acid probe, etc. (see for example, Sambrook and Russell, supra). One skilled in the art will appreciate which parameters to manipulate to optimize hybridization during hybridization-based reactions. In some hybridization-based reactions, however, such as polymerase reactions, amplification reactions, etc., the temperature of the reaction typically determines the stringency of the hybridization. Furthermore, the temperature also typically determines the stringency of the hybridization during in vivo reactions.

As used herein, the terms "identity" or "identical" refers to the extent that two nucleotide sequence or two amino acid sequences are the same when aligned for maximum correspondence. Optimal alignment and the percent identity between nucleotide sequences may be determined using the using the BLASTN algorithm of Altschul et al. (J. Mol. Biol. 215:403-410, 1990), and optimal alignment and the percent identity between two amino acid sequences may be determined using the BLASTP algorithm of Karlin and Altschul (Proc. Natl. Acad. Sci. USA 87:2264-2268, 1993). These algorithms are incorporated into the BLAST programs at the NCBI website (http://www.ncbi.nlm.nih.gov/BLAST/). To obtain gapped alignments for comparison purposes, Gapped BLAST may be utilized as described in Altschul et al. (Nucleic Acids Res. 25:3389-3402, 1997). When utilizing BLAST and Gapped BLAST programs, the default parameters of the respective programs are employed. The percentage of sequence identity is determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which an identical nucleotide occurs in both sequences to yield the number of matched positions, dividing the number of matched positions by the total number of positions in the window of comparison and multiplying the result by 100 to yield the percentage of sequence identity.

The term "nucleic acid" refers to molecules comprising deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos. The nucleotides may be linked by phosphodiester, phosphothioate, phosphoramidite, or phosphorodiamidate bonds.

"Sialidases" are a group of enzymes that catalyze the hydrolysis of terminal sialic acid residues from glycoconjugates, such as glycoproteins. Sialidases are also referred to as exo-a-sialidases, neuraminidases, or acetylneuraminidases.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the following examples represent techniques discovered by the inventors to function well in the practice of the invention. Those of skill in the art should, however, in light of the present disclosure, appreciate that many changes could be made in the specific embodiments that are disclosed and still obtain a like or similar result without departing from the spirit and scope of the invention, therefore all matter set forth is to be interpreted as illustrative and not in a limiting sense.

Example 1

Isolation of Additional Sialidase Genes in CHO Cells

Four sialidase genes (Neu1, Neu2, Neu3, and Neu4) have been identified and well-characterized in human, mouse, and rat. These sialidases exhibit different enzyme activities, substrate preferences, and subcellular locations. To date, however, only one sialidase gene has been characterized in CHO cells. This gene encodes a cytoplasmic sialidase (i.e., Neu2) (Gramer M J, Goochee C F. (1993) Biotechnol Prog, 9: 366). The purpose of this study was to determine whether CHO cells contain the other sialidase genes.

Using RT-PCR, 5'/3' RACE (rapid amplification of cDNA ends), and other standard methods, the other three sialidase genes were isolated and cloned from CHO cells. CHO Neu1 encoded a protein with 410 amino acid residues, and CHO Neu3 encoded a protein with 417 amino acid residues (Table 1). On the other hand, CHO Neu4 appeared to be a pseudogene in CHO cells. Both of Neu1 and Neu3 shared high similarities with their counterparts in other species (Table 2).

TABLE 1

Characteristics of New Sialidases in CHO Cells

| | cDNA | SEQ ID NO: | protein | SEQ ID NO: |
|---|---|---|---|---|
| Neu1 | 1463 bp | 1 | 410 aa | 2 |
| Neu3 | 1833 bp | 3 | 417 aa | 4 |

TABLE 2

Percent Similarity Between Sialidase Proteins.

| CHO Sialidases | Human Sialidases | Mouse Sialidases | Rat Sialidases |
|---|---|---|---|
| Neu1 (SEQ ID NO: 2) | 86.5% | 95.4% | 95.6% |
| Neu2 (SEQ ID NO: 5) | 77.1% | 86.5% | 87.1% |
| Neu3 (SEQ ID NO: 4) | 76.8% | 81.1% | 83.3% |

Example 2

CHO Neu1 and CHO Neu3 are Sialidases

Enzymatic sialidase activity studies were performed to confirm that the proteins coded by these two new genes having the expected functions in CHO cells. Briefly, the coding regions for the Neu1 (SEQ ID NO:1) and Neu3 (SEQ ID NO:3) genes, as well as the coding region of the previously reported Neu2 gene (Ferrari et al. (1994) Glycobiology 4(3): 367-373) were cloned into pcDNA3.1 mammalian expression vectors. The expression constructs then were transfected into COS7 cells to overexpress the sialidase proteins. The pcDNA3.1 vector alone was also transfected into COS7 cells as the mock transfection. An expression construct containing green fluorescence protein (GFP) was cotransfected into the COS7 cells to normalize the transfection efficiency.

Twenty-four hours after transfection, the cells were lysed by sonication. The cell debris was removed by centrifugation at 1000×g for 10 min at 4° C. and the supernatant factions were collected for enzymatic activity. The sialidase assay was performed as previously described (Gramer et al. (1993) Biotechnol Prog 9: 366-373) using 1 mM of 4-methylumbelliferone-Neu5Ac as substrate. For each lysate, 100 μg of protein was used in the assay. The assay was performed in triplicate. After normalization with the GFP readings, the CHO Neu1 and Neu3 proteins had significant sialidase activities (FIG. 1) as compared to the negative control (mock transfection) and the positive control (Neu2). In fact, the Neu3 protein had more than approximately 6-15 times as much activity as Neu2.

Figure 2:
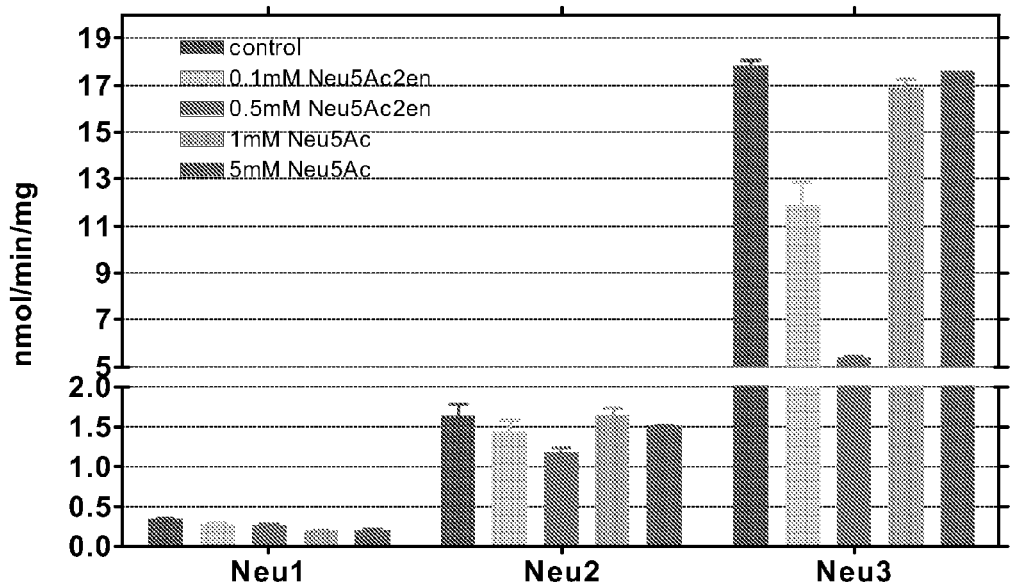
FIG. 2 illustrates the inhibition of the sialidase activity of proteins encoded by the CHO Neu1, Neu2, and Neu3 genes. Presented is the enzyme activity measured in the absence or presence of two concentrations of two different sialidase inhibitors in lysates of cells transfected with expression constructs containing the coding region of each gene.

To further examine the activity of these sialidase proteins, the sialidase assay was performed in the presence of two different sialidase inhibitors (Neu5Ac and Neu5AC2en) at two concentrations. As shown in FIG. 2, Neu5Ac2en had greater inhibitory effects than Neu5Ac on all the sialidases. Using CHO Neu3 as an example, 0.1 mM Neu3Ac2en decreased the activity about 30% and 0.5 mM Neu3Ac2en reduced the activity about 60%. These data indicate that the newly identified CHO genes (Neu1, and Neu3) code for sialidases.

Example 3

Subcellular Localization of CHO Sialidases

To identify the subcellular location for the two new CHO sialidases, immunocytochemistry with Confocal Scanning Microscopy technology was performed. Briefly, the Flag-tag encoding 8 amino acid residues (DYKDDDDK; SEQ ID NO:20) was cloned into the 3'-end of Neu expression constructs to express Flag-tagged fusion proteins. The Flag-tagged constructs were transfected into COS7 cells. Twenty-four hours after transfection, the cells were immunostained using standard procedures.

Figure 3:
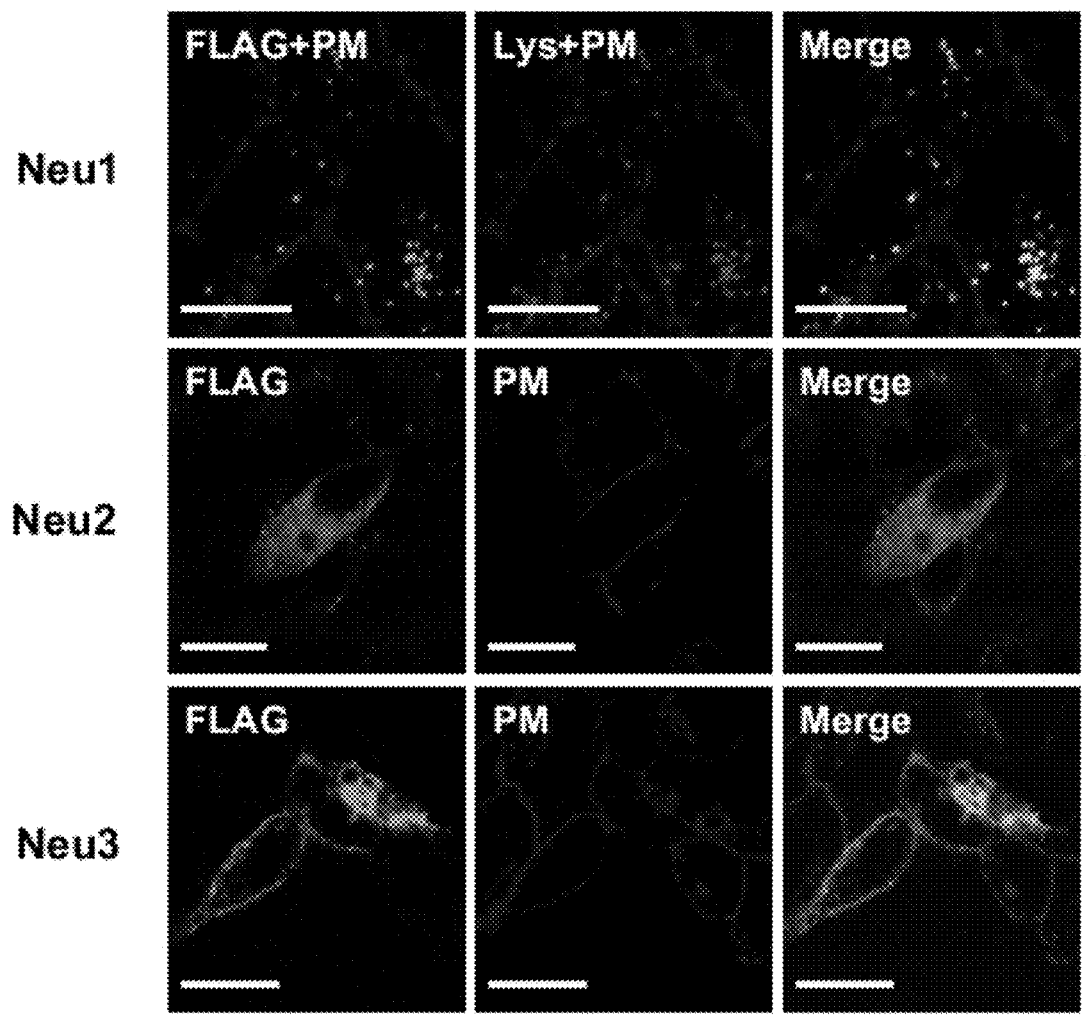
FIG. 3 presents the subcellular locations of the Neu1, Neu2, and Neu3 proteins. Presented are confocal fluorescence microscopy images in which the FLAG-tagged Neu proteins are shown in green, a lysosomal (Lys) marker is shown in red, and a plasma membrane (PM) marker is shown in blue.
Figure 4:
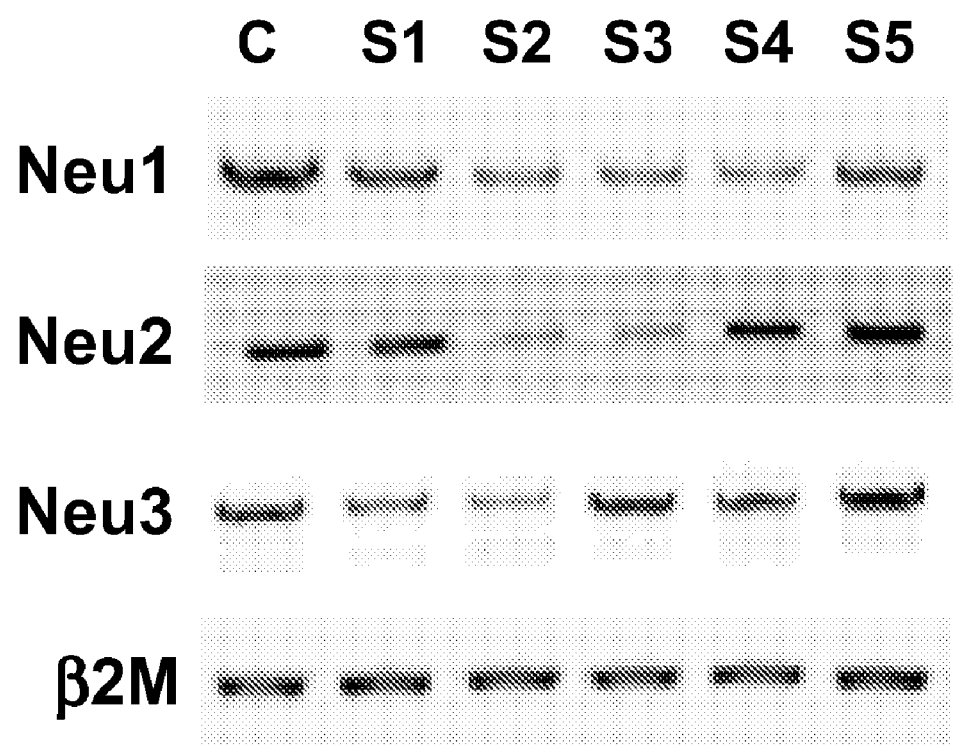
FIG. 4 illustrates knock down of the expression of the Neu1, Neu2, and Neu3 mRNAs using small interfering RNA (siRNA) technology. Presented are the products amplified via RT-PCR using gene specific primers after knockdown of each gene with gene specific siRNAs (S1-S5) or a control siRNA targeting an unrelated GFP nucleic acid sequence (C). The expression of a control gene (beta-2 microglubulin, β2M) was not affected by the siRNAs.
Figure 5:
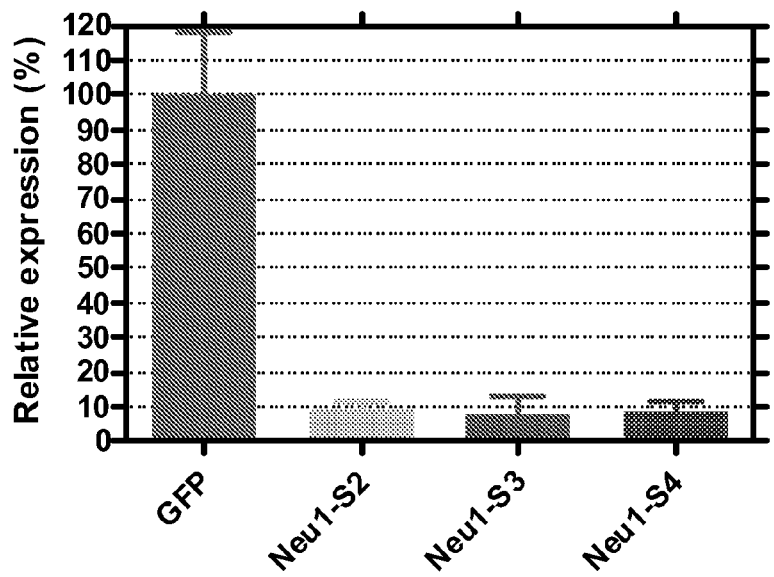
FIG. 5 illustrates knock down expression of (A) Neu1, (B) Neu2, and (C) Neu3 mRNA using small interfering RNA (siRNA) technology. Presented are the Q-RT PCR results showing the relative expression of each gene when using siRNAs specific for each Neu gene or a control siRNA targeting an unrelated nucleic acid sequence (GFP).
Figure 5:
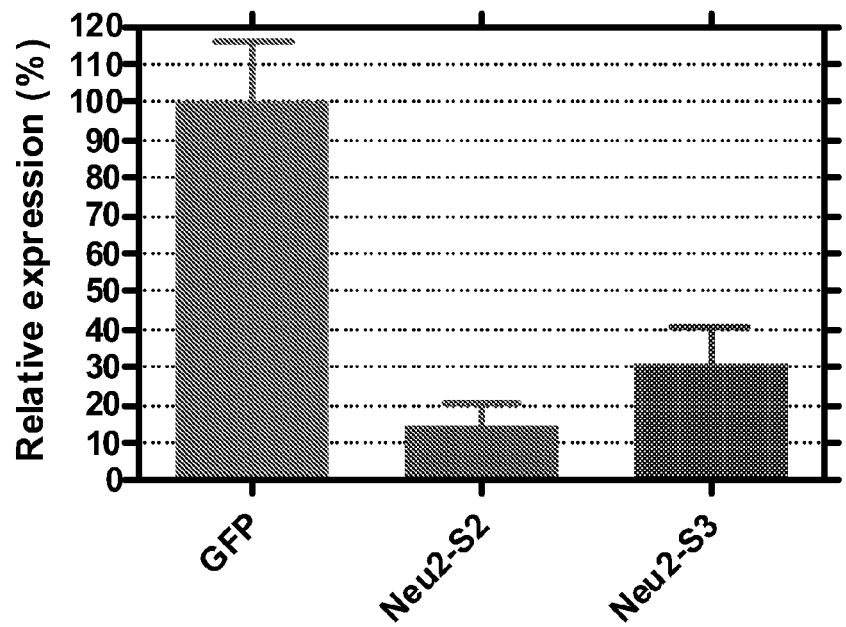
Figure 5C:
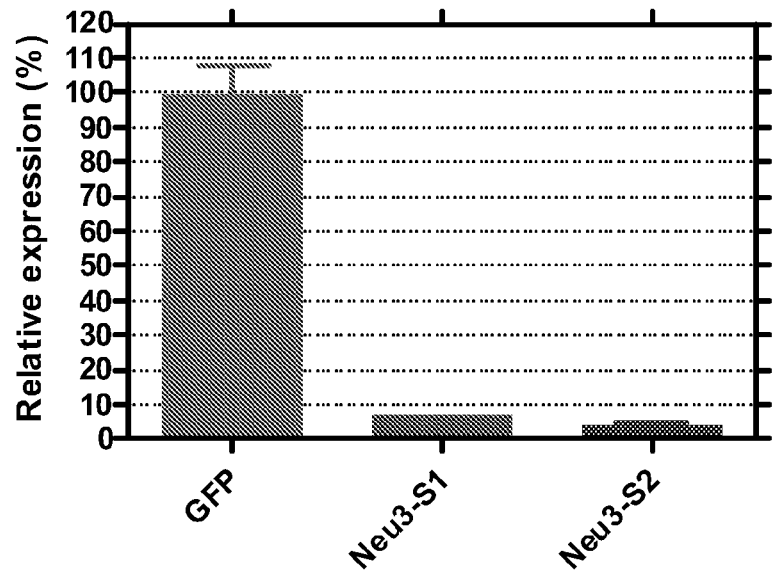

The results are presented in FIG. 3. The subcellular locations of the sialidases are indicated by the green fluorescence generated by the FITC-conjugated anti-FLAG antibody. The transfected cells were also immunostained with organelle markers: a lysosomal marker (LysoTracker DND-99), which is indicated by the red fluorescence and a plasma membrane marker (wheat germ agglutinin 647), which is indicated by the blue signal in the FIG. 3. This study revealed that Neu1 localized to lysosomes; its pattern of stain was nearly identical to that of the lysosomal marker. Neu3 localized to the plasma membrane, in a manner similar to that of the plasma membrane marker. Further, Neu2, the positive control, displayed cytoplasmic staining, as expected.

Example 4

Gene Silencing using siRNA Technology.

The expression of each of the three CHO sialidase genes was knocked down using small interfering RNA (siRNA) technologies. Based on the cDNA sequences, several siRNAs against the CHO sialidase genes (Neu1, Neu2, and Neu3) were designed and synthesized for each gene. The sequences are presented in Table 3. These siRNAs were transfected into a CHO cell line stably expressing human interferon gamma (CHO-hIFNγ). The transfections were performed in duplicate. Forty-eight hours after transfection, the cells were harvested. RNA and protein were isolated from the transfected cells. Reverse transcription polymerase chain reaction, (RT-PCR) and quantitative RT-PCR (Q-RT-PCR) using gene-specific primers were performed using standard procedures.

TABLE 3 siRNA Sequences.

| Gene | siRNA | Nucleotide sequence (5'-3')* | SEQ ID NO |
|------|-------|------------------------------|-----------|
| Neu1 | S2-sense | GGGUGCAAGACGACUUCAGtt | 6 |
|      | S2-antisense | CUGAAGUCGUCUUGCACCCtt | 7 |
|      | S3-sense | UGGGACGCUGGAACGAGAUtt | 8 |
|      | S3-antisense | AUCUCGUUCCAGCGUCCCAtt | 9 |
|      | S4-sense | GGACACUACGCGUCAUCUGtt | 10 |
|      | S4-antisense | CAGAUGACGCGUAGUGUCCtt | 11 |
| Neu2 | S2-sense | CCUGGGUGUGUACCUCAAUtt | 12 |
|      | S2-antisense | AUUGAGGUACACACCCAGGtt | 13 |
|      | S3-sense | GACGGAUGAGCAUGCAGAUtt | 14 |
|      | S3-antisense | AUCUGCAUGCUCAUCCGUCtt | 15 |
| Neu3 | S1-sense | GGGACCACCUACCGGAUUCtt | 16 |
|      | S1-antisense | GAAUCCGGUAGGUGGUCCCtt | 17 |
|      | S2-sense | GUACCAGCCGUGUGUUACUtt | 18 |
|      | S2-antisense | AGUAACACACGGCUGGUACtt | 19 |

*Upper case letters denote the 19 nt siRNA sequence and lower case letters denote the 3' overhang.

To identify the subcellular location for the two new CHO sialidases, immunocytochemistry with Confocal Scanning Microscopy technology was performed. Briefly, the Flag-tag encoding 8 amino acid residues (DYKDDDDK; SEQ ID NO:20) was cloned into the 3'-end of Neu expression constructs to express Flag-tagged fusion proteins. The Flag-tagged constructs were transfected into COS7 cells. Twenty-four hours after transfection, the cells were immunostained using standard procedures.

Figure 6:
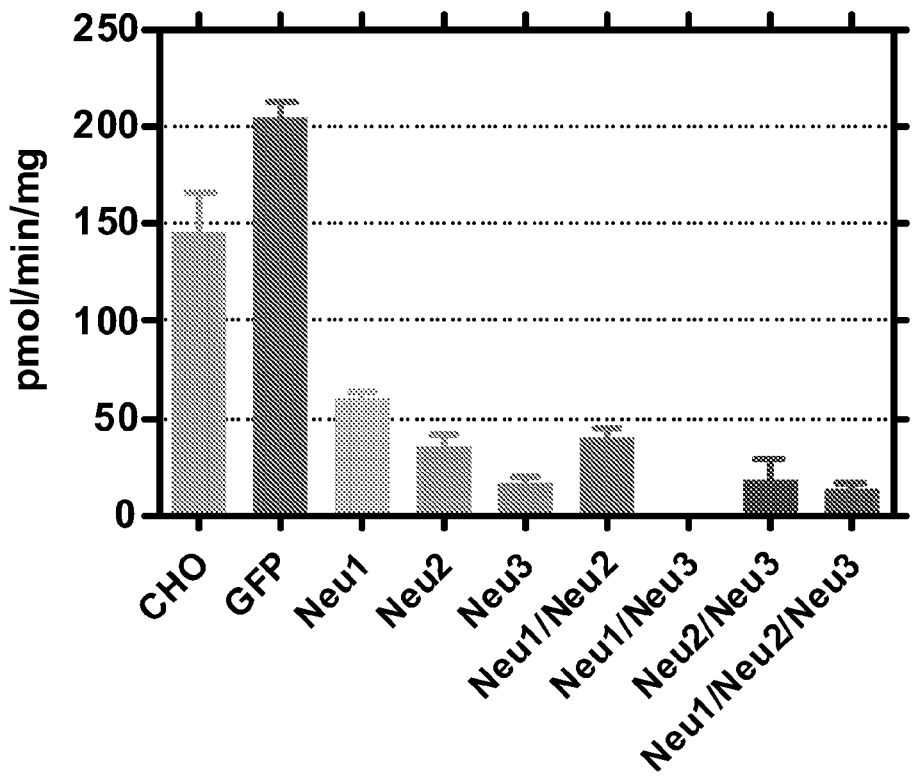
FIG. 6 illustrates the sialidase activity in CHO-hIFNγ cells in which Neu gene expression was knocked down using siRNAs. Presented is the sialidase activity in CHO-hIFNγ cells in which each Neu gene was silenced, two Neu genes were silenced, or all Neu genes were silenced. Also shown is the sialidase activity in CHO-hIFNγ cells that lacked siRNA constructs (CHO) or comprised a control siRNA targeting an unrelated nucleic acid sequence (GFP).

To further confirm the gene silencing effects at the protein level, a sialidase activity assay was performed. Adherent CHO-hIFNγ cells were suspended into a chemically defined and animal-component free medium. Positive siRNAs identified above were transfected by electroporation, in duplicate, into the suspension of CHO-hIFNγ cells. To investigate the potential synergistic gene silencing effects, each Neu gene was silenced individually and in combination (i.e., two or three genes were silenced). Seventy-two hours after transfection, the cells were harvested and washed with pre-chilled 1× PBS buffer. Total RNA and protein were separately isolated from the siRNA-transfected cells. Total RNA was used for reverse transcription (and Q-RT PCR) as described above. Protein was used for in vitro sialidase activity assays, as detailed in Example 2. Individual siRNA and siRNA combinations all significantly reduced the sialidase enzymatic activity compared to the controls (parental CHO-hIFNγ cells and GFP siRNA transfected cells) (FIG. 6). Most interestingly, the combination of siRNAs against Neu1 and Neu3 dramatically reduced sialidase activity to an undetectable level.

Example 5

Stable Gene Silencing using shRNA Technology

Based on the results in Example 4 showing that Neu mRNA and sialidase activity could be knocked down using siRNAs, Neu gene expression was stably knocked down in CHO hIFNγ cells using a shRNA technology platform (Mission: RNAi™, Sigma Aldrich, St. Louis, Mo.).

Figure 7:
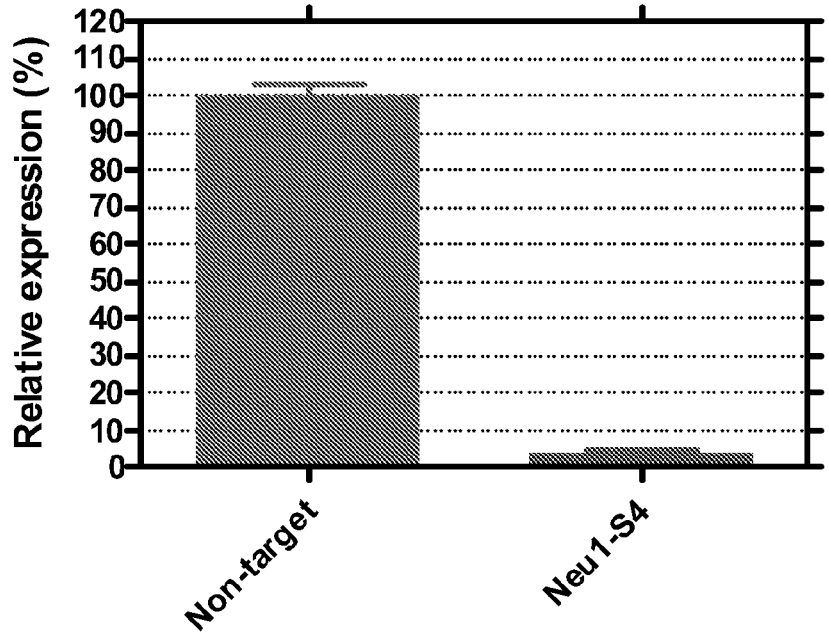
FIG. 7 illustrates stable knock down of (A) Neu1, (B) Neu2, and (C) Neu3 mRNA expression using short hairpin RNA (shRNA) technology. Presented are the Q-RT PCR results showing the relative expression of each sialidase gene in the corresponding knocked down CHO-hIFNγ cells or control CHO-hIFNγ cells (non-target), which comprised a control siRNA targeting an unrelated nucleic acid sequence.
Figure 7:
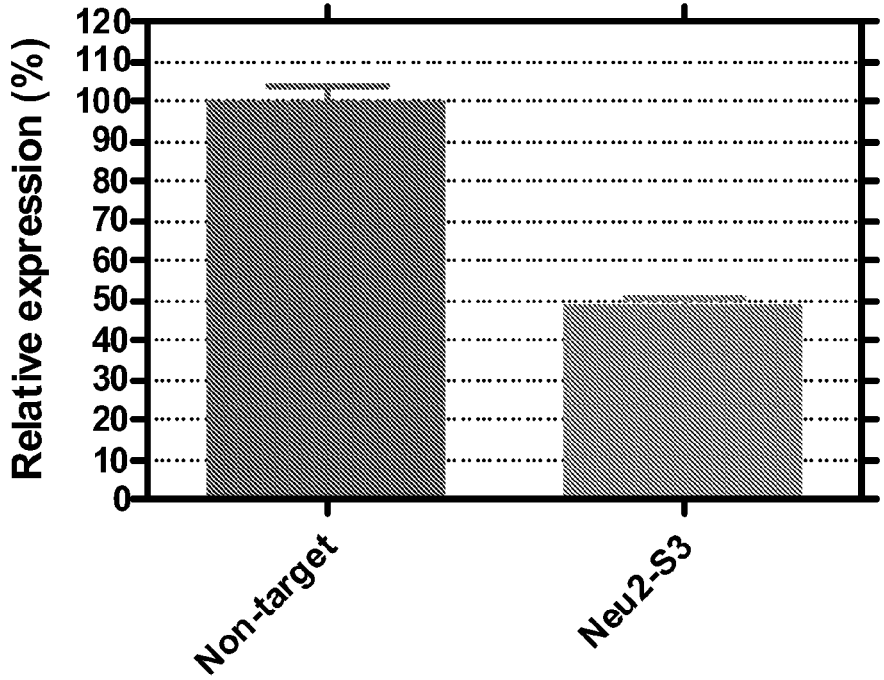
Figure 7C:
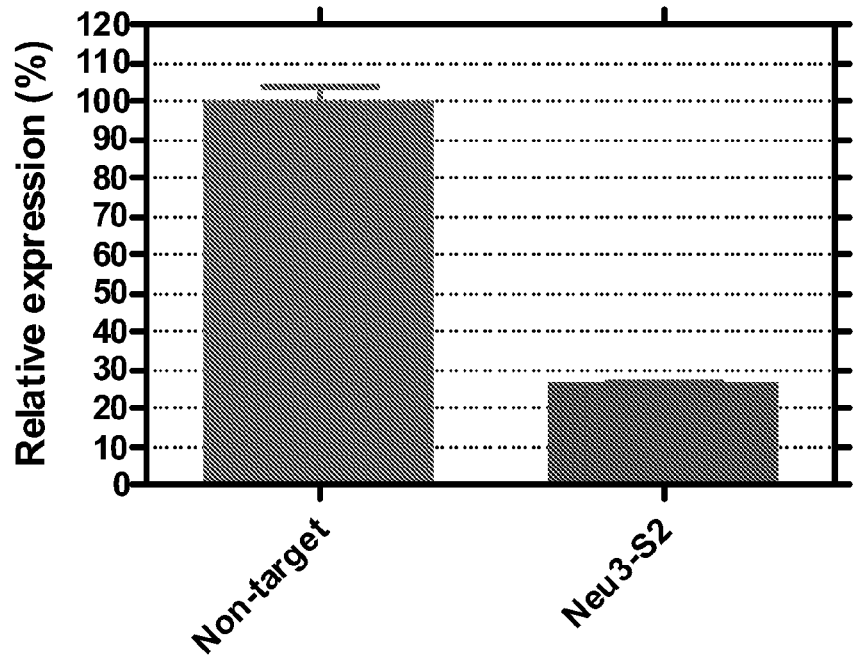

DNA fragments encoding the effective siRNAs for each sialidase gene (Neu1-S4, Neu2-S3, Neu3-S2) were cloned into the pLKO.1-puro shRNA expression vector. After DNA sequencing confirmation, plasmid DNAs were transfected into HEK293 cells to produce lentivirus packed with shRNA cassettes. After infection of suspension CHO-hIFNγ cells with lentivirus containing shRNA cassettes and puromycin selection, CHO-hIFNγ cells harboring shRNA cassettes for Neu1, Neu2 and Neu3 genes were obtained. Q-RT PCR was performed to confirm gene-silencing effects at the level of mRNA (FIG. 7). The mRNA expression knockdown of Neu1 (Neu1-S4) was over 95% in Neu1-shRNA cells (FIG. 7A), about 50% knockdown with Neu2 (Neu2-S3) in Neu2-shRNA cells (FIG. 7B), and over 70% knockdown with Neu3 (Neu3-S2) in Neu3-shRNA cells (FIG. 7C).

Figure 8:
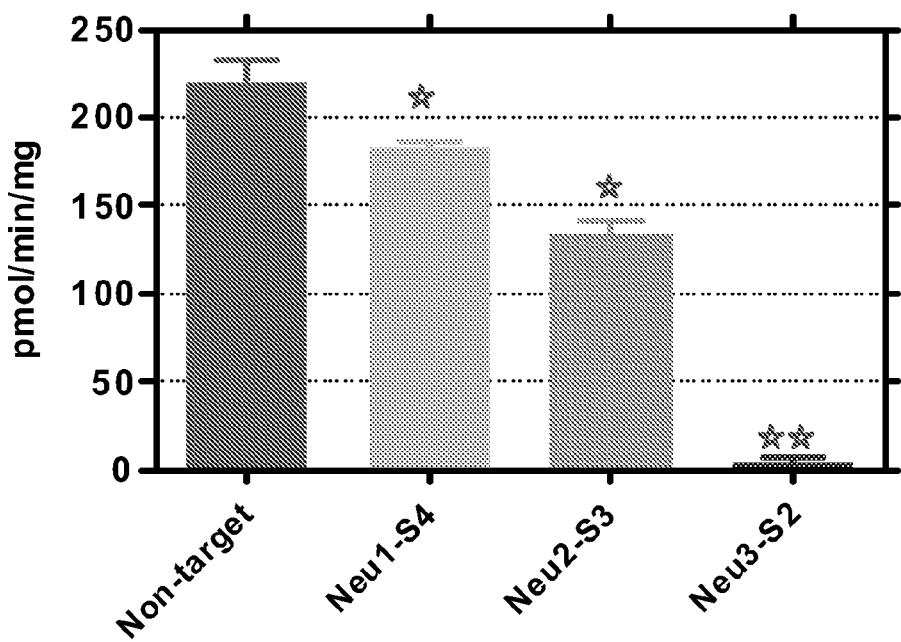
FIG. 8 illustrates the stable knock down of sialidase activity in CHO-hIFNγ cells using shRNAs. Presented is the sialidase activity in CHO-hIFNγ cells in which each of the sialidase genes (Neu1, Neu2, or Neu3) was silenced. Also shown is sialidase activity in control CHO-hIFNγ cells (non-target), which comprised a control shRNA targeting an unrelated nucleic acid sequence. *p<0.005, **p<0.0001.

Gene knockdown effects were also confirmed at the protein level by measuring sialidase activity as detailed above. Compared to the control (non-target shRNA), the shRNAs against all three sialidase genes significantly reduced the sialidase activity in CHO-hIFNγ cells (see FIG. 8). The cells harboring Neu3-S2 shRNA had the most dramatic reduction in sialidase activity.

To evaluate whether shRNAs affected cell growth and/or protein production, the growth of these CHO-shRNA cells and their production of human interferon gamma protein were analyzed. Briefly, cells were inoculated at ~200,000 cells/ml viable cell density in the culture medium (chemically defined and animal-component free) supplemented with 4 mM glutamine. The cell growth assay was set up in duplicate. Cells were cultured in 5 L bioreactors at 37° C., with 5% $CO_2$. At appropriate time points, samples of media were collected for protein analysis.

Figure 9:
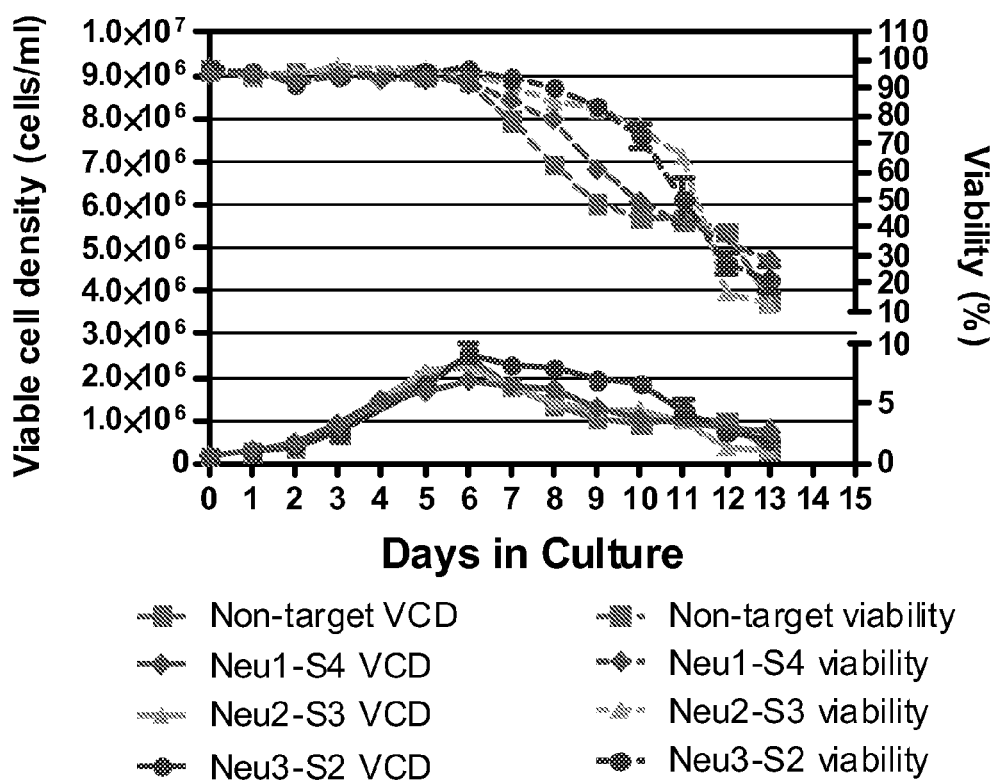
FIG. 9 illustrates that cell growth was not affected by sialidase gene silencing. Presented is cell growth (i.e., viable cell density (VCD) and percent viability) as a function of days in culture. Growth data are plotted for CHO-hIFNγ cells in which each sialidase gene (Neu1, Neu2, or Neu3) was knocked down or control (non-target) CHO-hIFNγ cells (which comprised a control shRNA targeting an unrelated nucleic acid sequence).
Figure 10:
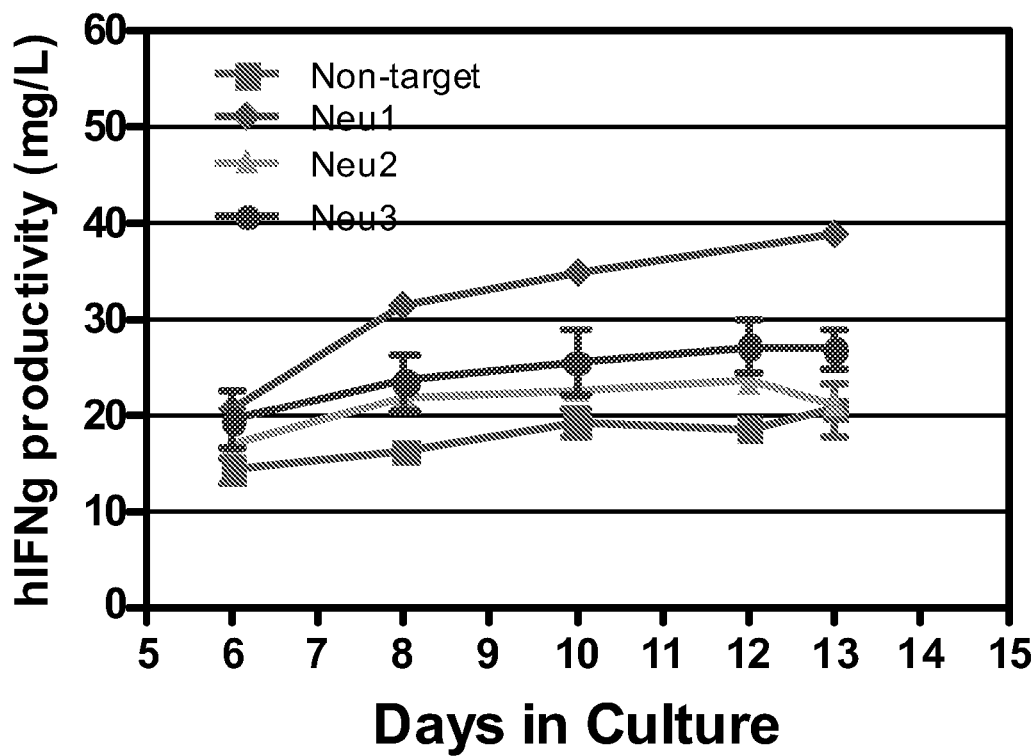
FIG. 10 illustrates that production of human interferon gamma (hIFNγ) was not affected by sialidase gene silencing. Plotted is the level of hIFNγ protein produced by CHO-hIFNγ cells in which each sialidase gene (Neu1, Neu2, or Neu3) was knocked down or control (non-target) CHO-hIFNγ cells.

The 5 L bioreactor cell growth data indicated that none of the shRNAs negatively affected cell growth as compared to the non-target shRNA control cells (FIG. 9). Production of human IFNγ was measured using an ELISA kit for human IFNγ (eBioscience, San Diego, Calif.). As shown in FIG. 10, none of the shRNAs negatively affected protein production as compared to the nontarget control cells. In fact, higher levels of human IFNγ protein were produced by some of the sialidase shRNA targeted cells. Similar results were obtained using 250-ml shaker flasks (data not shown).

Example 6

Silencing of CHO Neu Genes Produces Glycoproteins with Increased Sialic Acid Content The levels of sialic acid were analyzed by HPLC in human IFNγ protein produced by the sialidase shRNA targeted cells and non-target shRNA control cells. Spent media samples were collected from 5 L bioreactor cultures at stationary phase (day 6, cell viability around 95%) and death phase (day 13, cell viability around 20%). Human interferon gamma proteins were purified from cell culture supernatants by immunoaffinity purification. Briefly, after centrifugation and filtration to remove cell debris, 30 ml of a protein sample was loaded on an affinity column conjugated with hIFNγ antibody. After washing the column, hIFNγ protein was eluted with elution buffer. Purification was carried out on an AKTA Explorer 100 chromatographic system (Amersham Biosciences). The purified protein was quantified by ELISA as previously described.

The sialylation of purified hIFNγ proteins were analyzed by HPLC. Briefly, 50 μg of purified hIFNγ protein sample was lyophilized and resuspended in 100 μl of ultrapure water with 2N acetic acid. The sample was hydrolyzed at 80° C. for 3 hours. Then the sample was filtered and speed-vac dried. Released sialic acid residues were derivatized with a fluorogenic compound, 1,2-diamino-4,5-(methylenedioxy)benzene (DMB), followed by HPLC using C18 reverse phase column.

Figure 11A:
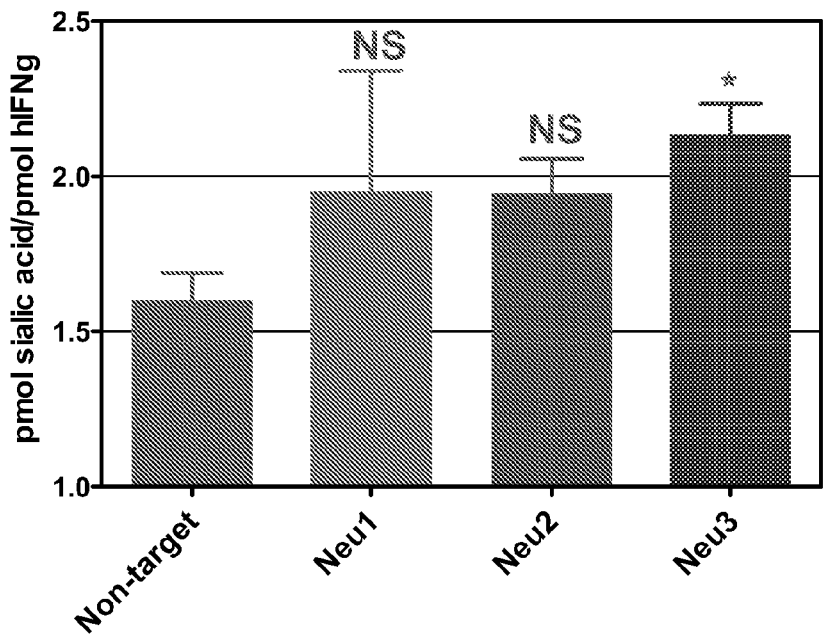
FIG. 11 illustrates that sialidase knocked down cells produce glycoproteins with increased levels of sialic acid. Plotted is the concentration of sialic acid in human interferon gamma (hIFNγ) produced by CHO-hIFNγ cells in which each sialidase gene (Neu1, Neu2, or Neu3) was knocked down or control (non-target) CHO-hIFNγ cells (which comprised a control shRNA targeting an unrelated nucleic acid sequence). NS, not significant, *p<0.01, **p<0.05.
Figure 11B:
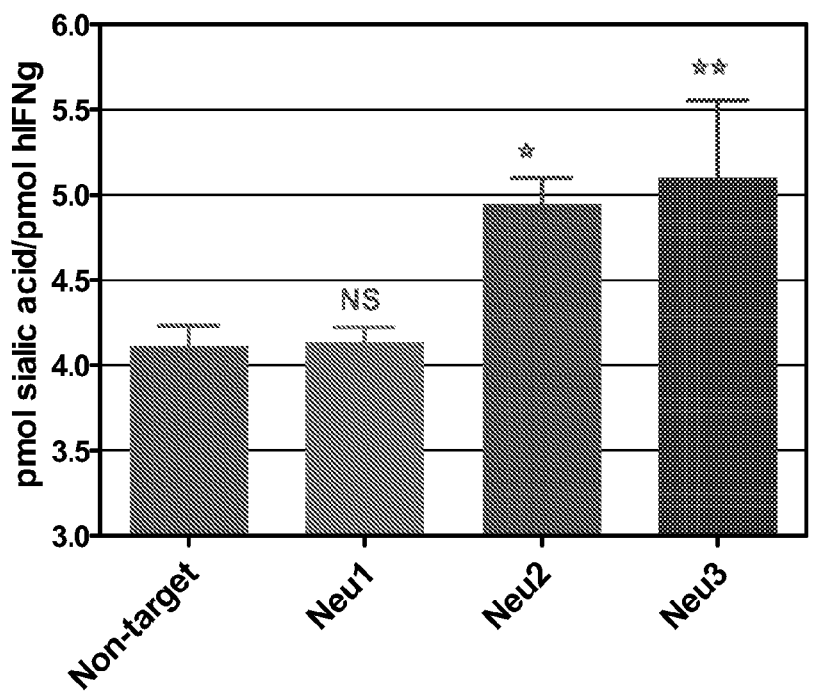

The data are presented in FIG. 11. On day 6, the levels of sialic acid in hIFNγ protein produced by Neu1 and Neu2 shRNA CHO cells were not significantly different from non-target shRNA control (FIG. 11A). Although the level of sialic acid appeared to be slightly higher in Neu2 shRNA cells, it was not significant (Neu2: 1.945±0.111 pmol sialic acid/pmol hIFNγ vs. non-target: 1.600±0.090 pmol sialic acid/pmol hIFNγ, p=0.0528, n=4). However, the sialic acid content of hIFNγ protein from Neu3 shRNA CHO cells was increased significantly comparing to protein from control cells (Neu3: 2.133±0.101 pmol sialic acid/pmol hIFNγ vs. non-target: 1.600±0.090 pmol sialic acid/pmol hIFNγ, p<0.01, n=4).

On day 13, there was no obvious improvement of sialylation with hIFNγ produced from Neu1 shRNA CHO cells. However, the levels of sialic acid were enhanced in hIFNγ protein produced by Neu2 cells (Neu2: 4.948±0.150 pmol sialic acid/pmol hIFNγ vs, non-target: 4.113±0.113 pmol sialic acid/pmol hIFNγ, p<0.01, n=4) and Neu3 cells (Neu3: 5.175±0.414 pmol sialic acid/pmol hIFNγ vs, non-target: 4.113±0.113 pmol sialic acid/pmol hIFNγ, p<0.05, n=4) (FIG. 11 B). The sialylation enhancement of human interferon gamma protein produced from Neu3 and Neu2 shRNA CHO cells indicates that the down-regulation of sialidase genes (Neu3 and Neu2) reduced overall sialidase activity and consequently reduced the levels of sialic acid in recombinant proteins produced by CHO cells. These examples demonstrate that targeted gene silencing using an RNA interference platform is an efficient way to improve protein glycosylation.

What is claimed is:

1. A cell line, the cell line comprising disrupted expression of at least one chromosomally integrated nucleic acid sequence encoding a non-cytoplasmic sialidase, the amino acid sequence of the non-cytoplasmic sialidase is (a) at least about 95% identical to SEQ ID NO:2, and/or (b) at least about 80% identical to SEQ ID NO:4.

2. The cell line of claim 1, wherein the amino acid sequence of the non-cytoplasmic sialidase is (a) at least about 97% identical to SEQ ID NO:2, and/or (b) at least about 90% identical to SEQ ID NO:4.

3. The cell line of claim 1, wherein the amino acid sequence of the non-cytoplasmic sialidase consists of SEQ ID NO:2 and/or SEQ ID NO:4.

4. The cell line of claim 1, wherein the expression of the nucleic acid sequence encoding the non-cytoplasmic sialidase is disrupted by a technique selected from the group consisting of RNA interference, homologous recombination, and site-specific recombination.

5. The cell line of claim 4, wherein RNA interference (RNAi) is mediated by an RNAi agent selected from the group consisting of short interfering RNA, a short hairpin RNA, and an RNAi expression vector.

6. The cell line of claim 1, wherein the cell line is selected from the group consisting of an insect cell line, a mammalian cell line, a rodent cell line, a non-human primate cell line, and a human cell line.

7. The cell line of claim 1, wherein the cell line is a Chinese hamster ovary (CHO) cell line.

8. The cell line of claim 7, wherein the amino acid sequence of the non-cytoplasmic sialidase consists of SEQ ID NO:2 and/or SEQ ID NO:4.

9. The cell line of claim 1, further comprising disrupted expression of a chromosomally integrated nucleic acid sequence encoding a cytoplasmic sialidase, the amino acid sequence of the cytoplasmic sialidase is at least about 85% identical to SEQ ID NO:5.

10. The cell line of claim 9, wherein the amino acid sequence of the cytoplasmic sialidase consists of SEQ ID NO:5.

11. The cell line of claim 9, wherein the expression of the nucleic acid sequence encoding the cytoplasmic sialidase is disrupted by a technique selected from the group consisting of RNA interference, homologous recombination, and site-specific recombination.

12. The cell line of claim 11, wherein RNA interference (RNAi) is mediated by an RNAi agent selected from the group consisting of short interfering RNA, a short hairpin RNA, and an RNAi expression vector.

13. The cell line of claim 9, wherein the cell line is selected from the group consisting of an insect cell line, a mammalian cell line, a rodent cell line, a non-human primate cell line, and a human cell line.

14. The cell line of claim 9, wherein the cell line is a Chinese hamster ovary (CHO) cell line.

15. The cell line of claim 14, wherein the amino acid sequence of the non-cytoplasmic sialidase consists of SEQ ID NO:2 and/or SEQ ID NO:4.

16. A method for producing a glycoprotein, the method comprising expressing a nucleic acid sequence encoding the glycoprotein in a cell comprising disrupted expression of at least one chromosomally integrated nucleic acid sequence encoding a non-cytoplasmic sialidase, the amino acid sequence of the non-cytoplasmic sialidase is (a) at least about 95% identical to SEQ ID NO:2, and/or (b) at least about 80% identical to SEQ ID NO:4, wherein the glycoprotein has increased sialylation relative to a suitable control.

17. The method of claim 16, wherein the amino acid sequence of the non-cytoplasmic sialidase is (a) at least about 97% identical to SEQ ID NO:2, and/or (b) at least about 90% identical to SEQ ID NO:4.

18. The method of claim 16, wherein the amino acid sequence of the non-cytoplasmic sialidase consists of SEQ ID NO:2 and/or SEQ ID NO:4.

19. The method of claim 16, wherein the expression of the nucleic acid sequence encoding the non-cytoplasmic sialidase is disrupted by a technique selected from the group consisting of RNA interference, homologous recombination, and site-specific recombination.

20. The method of claim 19, wherein RNA interference (RNAi) is mediated by an RNAi agent selected from the group consisting of short interfering RNA, a short hairpin RNA, and an RNAi expression vector.

21. The method of claim 16, wherein the nucleic acid sequence encoding the glycoprotein is chromosomally integrated or extrachromosomal.

22. The method of claim 16, wherein the cell is selected from the group consisting of an insect cell, a mammalian cell, a rodent cell, a non-human primate cell, and a human cell.

23. The method of claim 16, wherein the cell is a Chinese hamster ovary (CHO) cell.

24. The method of claim 23, wherein the amino acid sequence of the non-cytoplasmic sialidase consists of SEQ ID NO:2 and/or SEQ ID NO:4.

25. The method of claim 16, wherein the cell further comprises disrupted expression of a chromosomally integrated nucleic acid sequence encoding a cytoplasmic sialidase, the amino acid sequence of the cytoplasmic sialidase is at least about 85% identical to SEQ ID NO:5.

26. The method of claim 25, wherein the amino acid sequence of the cytoplasmic sialidase consists of SEQ ID NO:5.

27. The method of claim 25, wherein the expression of the nucleic acid sequence encoding the cytoplasmic sialidase is disrupted by a technique selected from the group consisting of RNA interference, homologous recombination, and site-specific recombination.

28. The method of claim 27, wherein RNA interference (RNAi) is mediated by an RNAi agent selected from the group consisting of short interfering RNA, a short hairpin RNA, and an RNAi expression vector.

29. The method of claim 25, wherein the cell is selected from the group consisting of an insect cell, a mammalian cell, a rodent cell, a non-human primate cell, and a human cell.

30. The method of claim 25, wherein the cell is a Chinese hamster ovary (CHO) cell.

31. The method of claim 30, wherein the amino acid sequence of the non-cytoplasmic sialidase consists of SEQ ID NO:2 and/or SEQ ID NO:4.

32. An isolated nucleic acid encoding a polypeptide whose amino acid sequence consists of SEQ ID NO:2 or SEQ ID NO:4.

* * * * *

UNITED STATES PATENT AND TRADEMARK OFFICE
CERTIFICATE OF CORRECTION

PATENT NO.           : 8,273,723 B2                                   Page 1 of 1
APPLICATION NO.      : 12/681699
DATED                : September 25, 2012
INVENTOR(S)          : Min Zhang et al.

It is certified that error appears in the above-identified patent and that said Letters Patent is hereby corrected as shown below:

Col. 18, line 54: "consequently reduced the levels of sialic" should read --consequently increased the levels of sialic--

Signed and Sealed this
Eighteenth Day of December, 2012

David J. Kappos
*Director of the United States Patent and Trademark Office*